(12) United States Patent
Sattler et al.

(10) Patent No.: US 12,030,845 B2
(45) Date of Patent: Jul. 9, 2024

(54) ISOMERIZATION OF NORMAL PARAFFINS

(71) Applicant: ExxonMobil Technology and Engineering Company, Annandale, NJ (US)

(72) Inventors: Wesley Sattler, Parsippany, NJ (US); Jihad M. Dakka, Whitehouse Station, NJ (US); Guang Cao, Princeton, NJ (US); Xinrui Yu, Furlong, PA (US); Brandon M. Carcuffe, Hackettstown, NJ (US); Jason M. Golias, Clinton, NJ (US); Scott J. Weigel, Allentown, PA (US); Carolyn M. Aimino, Milford, NJ (US); Megan E. Witzke, Bedminster, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/807,024

(22) Filed: Jun. 15, 2022

(65) Prior Publication Data
US 2022/0402838 A1 Dec. 22, 2022

Related U.S. Application Data

(60) Provisional application No. 63/202,585, filed on Jun. 17, 2021.

(51) Int. Cl.
*C07C 5/27* (2006.01)
*B01J 21/06* (2006.01)
(Continued)

(52) U.S. Cl.
CPC .......... *C07C 5/2705* (2013.01); *B01J 21/066* (2013.01); *B01J 23/002* (2013.01); *B01J 23/30* (2013.01);
(Continued)

(58) Field of Classification Search
CPC ............. C07C 5/2705; C07C 2521/06; C07C 2523/30; B01J 21/066; B01J 23/002; B01J 23/30; B01J 23/687; C10G 45/60
See application file for complete search history.

(56) References Cited

U.S. PATENT DOCUMENTS 4,956,514 A 9/1990 Chu
5,902,767 A 5/1999 Kresge et al.
(Continued)

*Primary Examiner* — Thuan D Dang
(74) *Attorney, Agent, or Firm* — Shook, Hardy & Bacon L.L.P.

(57) ABSTRACT

Isomerization of normal paraffins to form branched paraffins may be complicated by significant cracking of $C_{7+}$ paraffins under isomerization reaction conditions. This issue may complicate upgrading of hydrocarbon feeds having significant quantities of heavier normal paraffins. Cracking selectivity may be decreased by combining one or more naphthenic compounds with a feed mixture comprising at least one $C_{7+}$ normal paraffin and/or by utilizing tungstated zirconium catalysts having decreased tungsten loading. Further, $C_5$ and $C_6$ normal paraffins may undergo isomerization in the presence of $C_{7+}$ normal paraffins. Methods for isomerizing normal paraffins may comprise: providing a feed mixture comprising at least $C_5$-$C_7$ normal paraffins and lacking normal paraffins larger than $C_8$; and contacting the feed mixture with a bifunctional mixed metal oxide catalyst under isomerization reaction conditions effective to form a product mixture comprising one or more branched paraffins formed from each of the $C_5$-$C_7$ normal paraffins.

9 Claims, 22 Drawing Sheets

(51) Int. Cl.
*B01J 23/00* (2006.01)
*B01J 23/30* (2006.01)

(52) U.S. Cl.
CPC ...... *C07C 2521/06* (2013.01); *C07C 2523/30* (2013.01)

(56) References Cited

U.S. PATENT DOCUMENTS

| | | | |
|---|---|---|---|
| 6,080,904 | A | 6/2000 | Chang et al. |
| 6,124,232 | A | 9/2000 | Chang et al. |
| 6,162,757 | A | 12/2000 | Chang et al. |
| 6,706,659 | B2 | 3/2004 | Gillespie et al. |
| 7,399,896 | B2 | 7/2008 | Gillespie et al. |
| 2003/0069131 | A1 | 4/2003 | Ying et al. |
| 2011/0257007 | A1* | 10/2011 | Khurshid ................ B01J 23/58 502/308 |
| 2013/0324782 | A1 | 12/2013 | Shakun et al. |

\* cited by examiner

ISOMERIZATION OF NORMAL PARAFFINS

CROSS REFERENCE TO RELATED APPLICATIONS

This application claims priority to and the benefit of U.S. Ser. No. 63/202,585 filed on Jun. 17, 2021, the entire contents of which are incorporated herein by reference.

FIELD OF THE INVENTION

The present disclosure relates to paraffin isomerization and, more particularly, isomerization of normal paraffins under conditions that lead to decreased cracking selectivity.

BACKGROUND OF THE INVENTION

Isomerization of linear and monobranched paraffins (alkanes) to form more highly branched paraffins is frequently performed to improve octane rating. Paraffin isomerization to form more highly branched alkanes may be realized using a bifunctional catalyst, such as a mixed metal oxide. Without being bound by theory or mechanism, such catalysts are believed to promote paraffin isomerization through dehydrogenation, protonation to form a carbenium ion, and skeletal rearrangement of the carbenium ion through mechanisms such as those involving a cyclopropyl cation.

In conventional paraffin isomerization processes, a paraffin feed mixture is heated in the presence of hydrogen and a suitable bifunctional catalyst. U.S. Patent Application Publication 2013/0324782 describes one such example of a conventional paraffin isomerization process utilizing a bifunctional catalyst. U.S. Pat. Nos. 6,080,904 and 6,124,232 provide additional details of bifunctional catalysts that are acidic metal oxide catalysts, and paraffin isomerization processes conducted therewith. C5 and C6 normal (linear) paraffins may undergo isomerization readily in such processes. Catalysts such as chlorided alumina, sulfated zirconia, and zeolites may be utilized for isomerizing C5 and C6 paraffins with high selectivity against cracking. C7+ normal paraffins, in contrast, become increasingly prone to cracking under the isomerization reaction conditions, particularly at higher reaction temperatures and conversion percentages of the feed mixture, even in the presence of tungstated zirconium catalysts that are less prone to producing cracking. Excessive cracking leads to yield loss of the desired branched paraffins. As such, isomerization reactions may be run at low temperatures where cracking is not as problematic, albeit at the expense of poor feed conversion. Without being bound by any theory or mechanism, cracking is believed to occur through β-scission of the cyclopropyl carbenium cation intermediate. During β-scission, carbenium cations formed from C5 and C6 normal paraffins lead to formation of an ethyl cation, a primary carbenium ion that forms with difficulty. In contrast, C7+ paraffins may form more stable and more easily generated secondary or tertiary carbenium ions upon β-scission. As such, it can sometimes be difficult to mitigate cracking of C7+ paraffins under isomerization reaction conditions, especially at high feed conversion.

As branched hydrocarbons having higher octane ratings are generally desirable as blending components for the manufacture of premium gasolines, conventional isomerization processes are not particularly efficient for increasing the octane number of C7+ normal paraffins, such as those obtained from shale oil naphtha and other light naphthas, given their tendency to undergo extensive cracking instead. Catalytic reforming is also not a particularly desirable option for processing light naphthas due to the rather low energy efficiency of such processes and the frequent low starting aromatic content of this hydrocarbon resource. This difficulty is especially true for the smaller normal paraffin components of light naphthas (e.g., C5-C7 normal paraffins). Catalytic reforming may be a more favorable option for heavier naphthas (e.g., C8+ normal paraffins and other hydrocarbons). Thus, there is still not an effective way to process the entirety of a naphtha stream to form branched paraffins having a high octane number, particularly the C5-C7 normal paraffin components of light naphthas, given their propensity to undergo cracking.

SUMMARY OF THE INVENTION

In some aspects, paraffin isomerization methods comprise: providing a feed mixture comprising at least C5-C7 normal paraffins; and contacting the feed mixture with a bifunctional mixed metal oxide catalyst under isomerization reaction conditions effective to form a product mixture comprising one or more branched paraffins formed from each of the C5-C7 normal paraffins.

In some aspects, paraffin isomerization methods comprise: providing a bifunctional mixed metal oxide catalyst comprising a bifunctional mixed metal oxide impregnated with a noble metal; wherein the bifunctional mixed metal oxide catalyst comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater; contacting the bifunctional mixed metal oxide catalyst under the isomerization reaction conditions with a feed mixture comprising at least one C7+ normal paraffin; and obtaining one or more branched paraffins formed from the at least one C7+ normal paraffin under the isomerization reaction conditions.

In some aspects, paraffin isomerization methods comprise: providing a feed mixture comprising at least one C7+ normal paraffin; combining a co-feed comprising one or more naphthenic compounds with the feed mixture; and contacting the feed mixture and the co-feed with a bifunctional mixed metal oxide catalyst under isomerization reaction conditions effective to form a product mixture comprising one or more branched paraffins formed from the at least one C7+ normal paraffin; wherein a cracking selectivity of the at least one C7+ normal paraffin under the isomerization reaction conditions is about 15 wt. % or less, based on a total weight of the feed mixture.

In some aspects, compositions for promoting isomerization of normal paraffins comprise: a bifunctional mixed metal oxide impregnated with a noble metal, the bifunctional mixed metal oxide comprising tungsten, zirconium, and a variable oxidation state metal; wherein the bifunctional mixed metal oxide comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane under isomerization reaction conditions to one or more branched paraffins at about 70% to about 80% conversion with a selectivity ratio of conversion to cracking for n-heptane of about 11 or greater.

In some aspects, paraffin isomerization methods using two bifunctional mixed metal oxide catalysts in sequence comprise: providing a first bifunctional mixed metal oxide catalyst and a second bifunctional mixed metal oxide catalyst, each bifunctional mixed metal oxide catalyst being impregnated with a noble metal; wherein the second bifunctional mixed metal oxide catalyst comprises about 40 wt. % to about 70 wt. % zirconium and about 0.01 wt. % to about 5 wt. % variable oxidation state metal, each based on total mass of the mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater, and the first bifunctional mixed metal oxide catalyst comprises about 40 wt. % to about 70 wt. % zirconium and about 0.01 wt. % to about 5 wt. % variable oxidation state metal, each based on total mass of the mixed metal oxide, and an amount of tungsten that is higher than that present in the second bifunctional mixed metal oxide catalyst; sequentially contacting the first bifunctional mixed metal oxide catalyst and the second bifunctional mixed metal oxide catalyst, each impregnated with the noble metal, under the isomerization reaction conditions with a feed mixture comprising at least one C7+ normal paraffin; and obtaining one or more branched paraffins formed from the at least one C7+ normal paraffin under the isomerization reaction conditions.

In some aspects, methods for upgrading naphtha comprise: separating a naphtha stream into a high boiling point fraction comprising C8+ hydrocarbons, and a low boiling point fraction comprising C8− hydrocarbons; and contacting the low boiling point fraction with a bifunctional mixed metal oxide catalyst under isomerization reaction conditions effective to form a product mixture comprising one or more branched paraffins.

These and other features and attributes of the disclosed methods and compositions of the present disclosure and their advantageous applications and/or uses will be apparent from the detailed description which follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

To assist one of ordinary skill in the relevant art in making and using the subject matter hereof, reference is made to the appended drawings, wherein.

DETAILED DESCRIPTION OF THE INVENTION

Figure 1:
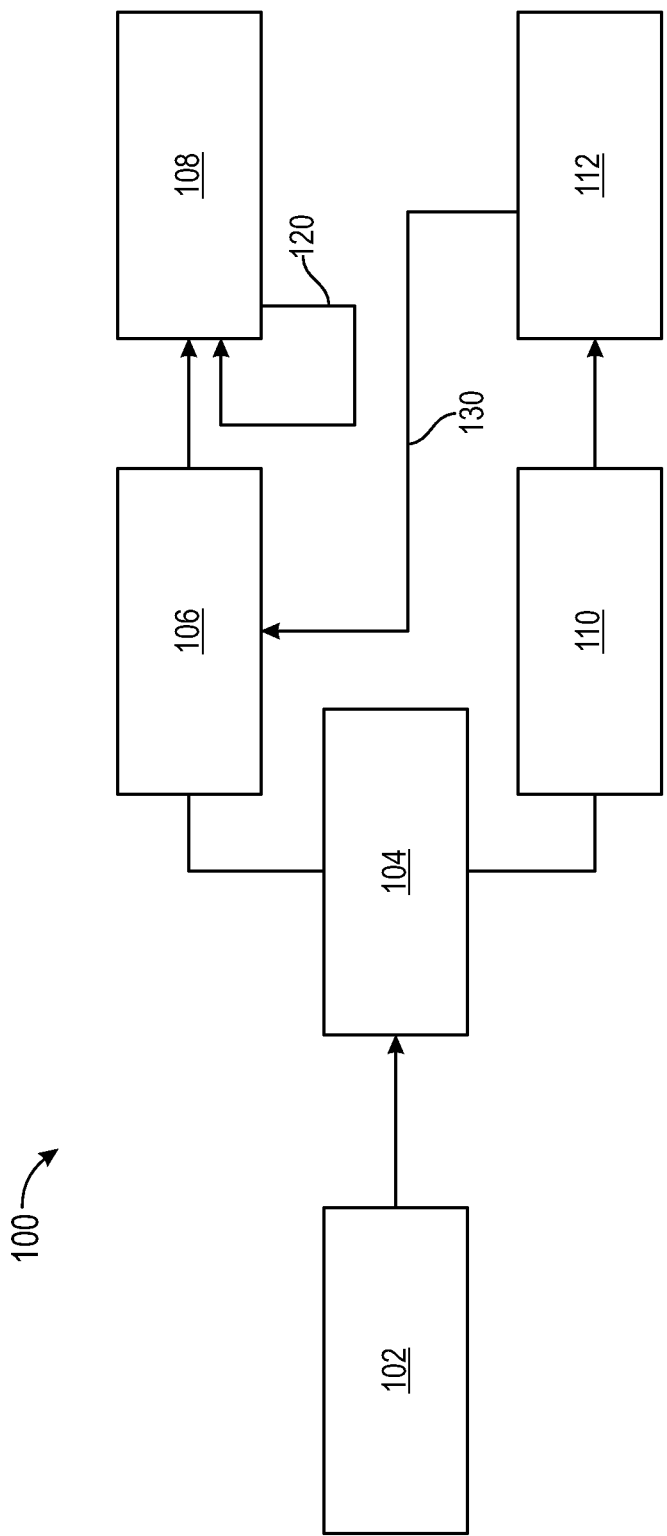
FIG. 1 is an illustrative process flow diagram showing how a naphtha stream may be separated and processed according to the disclosure herein.

The present disclosure relates to isomerization of paraffin compounds and, more particularly, isomerization of normal paraffins under conditions that lead to improved processing efficiency and decreased cracking selectivity for C7+ normal paraffins.

As discussed above, isomerization of normal paraffins may be conducted to increase octane number, but excessive cracking of C7+ paraffins, particularly normal paraffins in this size range, may be problematic in various respects. To combat the favorability of cracking C7+ paraffins, isomerization may be conducted at lower temperatures and lower feed mixture conversions, which may be undesirable from a processing efficiency standpoint. As such, it may be difficult to upgrade the octane number of hydrocarbon resources having a significant fraction of normal paraffins. In particular, it may be difficult to process both the light naphtha and heavy naphtha components of a naphtha stream in an efficient manner.

Depending on the boiling point cut taken during distillation of a naphtha stream, C7 and C8 normal paraffins may reside in either a light naphtha fraction or a heavy naphtha fraction. If residing predominantly in the heavy naphtha fraction, the C7 normal paraffins may undergo less effective catalytic reforming than do C8+ normal paraffins. If residing in the light naphtha fraction, C7 and C8 normal paraffins may be susceptible to cracking, as discussed above.

The present disclosure provides a number of complementary approaches for processing feed mixtures possessing a significant fraction of normal paraffins, particularly normal paraffins that are susceptible to undergoing cracking under typical isomerization reaction conditions. In various aspects, the present disclosure provides for separation of a naphtha stream into a light naphtha fraction comprising C8− normal paraffins, such as C7− normal paraffins, and a heavy naphtha fraction comprising C8+ normal paraffins. The heavy naphtha fraction may undergo subsequent catalytic reforming, and the light naphtha fraction may be separately exposed to isomerization reaction conditions. This approach may limit the amount of C7+ normal paraffins, especially C8+ normal paraffins, that are exposed to isomerization reaction conditions that may also promote cracking of normal paraffins in this size range, while also providing a more effective feed mixture for catalytic reforming.

Additionally, the light naphtha fraction may undergo isomerization under isomerization reaction conditions that are less prone to promoting cracking than are conventional isomerization reaction conditions. In one aspect, bifunctional mixed metal oxide catalysts, such as tungstated zirconium catalysts, promoting a decreased extent of cracking may be employed. In another aspect, naphthenic compounds may be introduced to the light naphtha fraction, which may decrease the extent to which cracking occurs during isomerization. The bifunctional mixed metal oxide catalysts producing decreased cracking and the naphthenic compounds may be utilized separately to promote decreased cracking, or they may be implemented in combination with one another. Moreover, the bifunctional mixed metal oxide catalysts and the naphthenic compounds may be utilized separately or together to mitigate cracking of C7+ normal paraffins without first separating a naphtha stream into a light naphtha fraction and a heavy naphtha fraction. Likewise, a heavy naphtha fraction separated from C5-C7 light naphtha hydrocarbons need not necessarily undergo catalytic reforming in combination with the isomerization methods disclosed herein. Concurrent catalytic reforming may allow a hydrocarbon feed mixture to be more effectively and completely utilized, however.

In another surprising aspect of the present disclosure, isomerization of C5 and C6 normal paraffins may take place with increased yield in the presence of at least C7 normal paraffins. Thus, a light naphtha fraction containing C5-C7 normal paraffins may be isomerized more effectively as a mixture rather than being further separated into individual normal paraffin components (e.g., C5, C6 and C7) and then processing each individual normal paraffin component separately. Moreover, cracking of C7 normal paraffins may decrease in a mixture of C5-C7 normal paraffins compared to the cracking obtained during isomerization of C7 normal paraffins alone, but without concurrently decreasing the isomerization yield of the C7 normal paraffins. Isomerization of a mixture of C5-C7 normal paraffins may be further enhanced, if needed, by utilizing a bifunctional mixed metal oxide catalyst capable of affording decreased cracking and/or naphthenic compounds to suppress cracking as well.

Accordingly, the various aspects of the present disclosure may allow a wider breadth of components in a hydrocarbon feed mixture to be processed more effectively. That is, the present disclosure may provide a feed mixture more suitable for catalytic reforming to produce aromatic compounds while also affording a feed mixture more amenable for isomerization, especially with a decreased extent of cracking at high conversion during isomerization. Singular or combined approaches may facilitate isomerization without an excessive degree of cracking taking place, as described further herein.

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature) is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18.

As used herein, the term "hydrocarbon" refers to (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecular structure having n total carbon atom, or (ii) any mixture of two or more such hydrocarbon compounds in (i). Any degree of unsaturated may be present in such Cn hydrocarbons. Thus, a C2 hydrocarbon may refer to ethane, ethylene, acetylene, or mixtures of at least two of these hydrocarbons at any proportion. The term "Cn+ hydrocarbon" means (i) any hydrocarbon compound comprising n or greater carbon atom(s) in its molecular structure, or (ii) any mixture of two or more such hydrocarbon compounds in (i). The term "Cn− hydrocarbon" means (i) any hydrocarbon compound comprising n carbon atoms or less in its molecular structure, or (ii) any mixture of two or more such hydrocarbon compounds in (i).

As used herein, the term "naphtha" refers to a hydrocarbon resource comprising at least C4-C12 hydrocarbons, particularly C4-C12 saturated hydrocarbons.

As used herein, the term "light naphtha" refers to a hydrocarbon resource comprising predominantly C8− hydrocarbons. C8− hydrocarbons may include light naphthas containing C5-C7 normal paraffins and optionally C8 normal paraffins.

As used herein, the term "heavy naphtha" refers to a hydrocarbon resource comprising predominantly C8+ hydrocarbons. The term "C8+ hydrocarbons" refers to any hydrocarbon containing 8 carbon atoms or more. C8+ hydrocarbons may include heavy naphthas containing C8-C12 normal paraffins and optionally up to C30 normal paraffins.

As used herein, the terms "paraffin," "alkane" and "saturated hydrocarbon" are synonymous with one another and refer to hydrocarbons having a formula of $C_nH_{2n+2}$.

As used herein, the terms "linear" and "normal" are synonymous with one another and refer to hydrocarbons without side-chain branches.

As used herein, the term "cracking" refers to the conversion of a given hydrocarbon molecule into two or more smaller hydrocarbon molecules. Cracking yield may be determined by the mass of smaller hydrocarbons produced upon isomerizing a larger hydrocarbon. For example, when isomerizing a C5+ alkane feed mixture, the cracking yield may represent the yield of C1-C4 hydrocarbons produced upon isomerization.

As used herein, the term "isomerization" refers to a skeletal rearrangement of a hydrocarbon, particularly conversion of a normal paraffin into a branched paraffin.

As used herein, the term "weight hour space velocity" (WHSV) refers to a measure of the weight of a feed mixture flowing per unit weight of a catalyst per hour.

As used herein, the term "liquid hour space velocity" (LHSV) refers to a measure of the volume of a feed mixture flowing per unit volume of a catalyst per hour.

As used herein, the term "variable oxidation state metal" refers to a metal having two or more accessible oxidation states other than a zero oxidation state.

As used herein, the term "total surface area" refers to the total specific external and internal surface area of disperse or porous solids (microporous materials), which is obtained by measuring the amount of physically adsorbed N2 adsorption/desorption isotherms, such as specified in ISO 9277.

As used herein, the term "ammonia uptake" refers to the measurement of temperature programmed ammonia desorption of disperse or porous solids (microporous materials), which is measured as described in Applied Catalysis A: General, 1997, 165, 57-72.

As used herein, the term "digestion" refers to a thermal treatment taking place by heating a solid in a solvent in which an impurity species may be soluble but the majority of the solid is not. Digestion may allow for equilibration of species to take place, along with ripening of particles of the insoluble solid. The digestion conditions, including the digestion temperature, may impact the surface area and the porosity of a mesoporous material obtained therefrom.

In various embodiments, methods of the present disclosure may comprise providing a feed mixture comprising at least C5-C7 normal paraffins (and optionally C8 normal paraffins) and lacking normal paraffins larger than C8, and contacting the feed mixture with a bifunctional mixed metal oxide catalyst under isomerization reaction conditions effective to form a product mixture comprising one or more branched paraffins formed from each of the C5-C7 normal paraffins (and optionally C8 normal paraffins). Suitable bifunctional mixed metal oxide catalysts and isomerization reaction conditions are specified in further detail below. In some embodiments, an extent of conversion of C5 and C6 normal paraffins under the isomerization reaction conditions in a presence of C7 normal paraffins may be greater than an extent of conversion obtained with C5 or C6 normal paraffins are contacted with the bifunctional mixed metal oxide catalyst in an absence of C7 normal paraffins under the isomerization reaction conditions. The presence of the C5 and/or C6 normal paraffins may also at least partially suppress cracking of C7+ normal paraffins as well.

Any bifunctional mixed metal oxide catalyst effective to promote isomerization of a normal paraffin may be utilized in the disclosure herein. Suitable bifunctional mixed metal oxide catalysts may include an acidic solid oxide of a Group 4 metal, such as Ti or Zr, modified with an anion or oxyanion of a Group 6 metal, such as Mo or W. Optionally, a variable oxidation state metal may also be present, such as Fe, Mn, Co, Ce, Cu, Ni, or any combination thereof. The variable oxidation state metal may cycle between a +2/+3 oxidation state or a +3/+4 oxidation state. The bifunctional mixed metal oxide catalyst may be prepared by co-precipitation, calcination and extrusion to form catalyst particles in a suitable shape. U.S. Pat. Nos. 4,956,514; 5,902,767; and 6,162,757, each incorporated herein by reference in their entirety, provide additional details regarding suitable bifunctional mixed metal oxide catalysts and methods for their production. The bifunctional mixed metal oxide catalyst may be further impregnated with a Group 8 or 9 metal or a Group 10 metal (noble metal), such as Pt or Pd, such as through incipient wetness or vacuum infiltration.

Particularly suitable bifunctional mixed metal oxide catalysts for promoting a low extent of cracking may comprise Zr as the Group 4 metal and W as the Group 6 metal. Such bifunctional mixed metal oxide catalysts may be referred to as tungstated zirconium oxide catalysts herein, which may comprise about 5 wt. % to about 25 wt. % W, about 40 wt. % to about 70 wt. % Zr, and about 0.01 wt. % to about 5 wt. % variable oxidation state metal, such as Fe, each based upon total mass of the bifunctional mixed metal oxide catalyst. In some embodiments, the molar ratio of Group 4 metal to variable oxidation state metal may range from about 10 to about 500, inclusive of any value or subrange in between. Once impregnated with a Group 8-10 metal, such tungstated zirconium oxide catalysts may comprise about 0.01 wt. % to about 2 wt. % Group 8-10 metal or about 0.001 wt. % to about 5 wt. % Group 8-10 metal, such as a noble metal (e.g., Pt), based upon total mass of the bifunctional mixed metal oxide catalyst.

In some examples, the bifunctional mixed metal oxide catalyst may comprise a Fe-containing $(WO_3)x/(ZrO_2)y$ catalyst impregnated with a noble metal, such as Pt. The molar ratio of y:x may range from about 2 to about 100 or about 1 to about 5, encompassing any value and subset therebetween. Suitable bifunctional mixed metal oxide catalysts are discussed, for example, in U.S. Pat. Nos. 5,902,767; 6,706,659; 7,399,896; and U.S. Patent Application Publication 2003/0069131, each of which is incorporated herein by reference in its entirety.

Some examples of the bifunctional mixed metal oxide catalysts may be effective to promote isomerization of n-heptane (C7 normal paraffins) with a decreased degree of cracking. Such bifunctional mixed metal oxide catalysts may comprise: a mixed metal oxide impregnated with a noble metal, the mixed metal oxide comprising tungsten, zirconium, and a variable oxidation state metal. The mixed metal oxide may be prepared by co-precipitation, calcination and extrusion to form catalyst particles in a suitable shape. The tungsten loading of the bifunctional mixed metal oxide catalysts may be regulated to control the cracking yield for n-heptane. The mixed metal oxide may comprise about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater. Suitable variable oxidation state metals may include, for example, Fe, Mn, Co, Cu, Ce, Ni, and any combination thereof. In a particular example, the variable oxidation state metal may be Fe.

In more specific embodiments, bifunctional mixed metal oxide catalysts capable of promoting decreased n-heptane cracking under isomerization reaction conditions may feature a selectivity ratio ranging from about 11 to about 14, or about 11.5 to about 13.5, or about 12 to about 13. At these selectivity ratios, the amount of tungsten may be effective to afford a cracking yield for n-heptane of about 10 wt. % or less, or about 9 wt. % or less, or about 8 wt. % or less, or about 7 wt. % or less, or about 6 wt. % or less, or about 5 wt. % or less, or about 4 wt. % or less, or about 3 wt. % or less, or about 2 wt. % or less, or about 1 wt. % or less, including a cracking yield for n-heptane at about 70% to about 80% conversion of about 5 wt. % to about 7 wt. %. According to various embodiments, the bifunctional mixed metal oxide catalyst may promote conversion to about 70% to about 80%, or about 80% to about 90%, or about 90% to about 95%.

In more specific examples, contacting the bifunctional mixed metal oxide catalyst with the feed mixture under the isomerization reaction conditions may afford about 95% or less conversion of one or more C7+ normal paraffins in the feed mixture. Alternately, the isomerization reaction conditions may afford about 90% or less conversion, or about 85% or less conversion, or about 80% or less conversion, or about 75% or less conversion of one or more C7+ normal paraffins in the feed mixture. In one example, the isomerization reaction conditions may afford about 70% to about 80% conversion, or about 80% to about 90%, or about 90% to about 95% of the at least one C7+ normal paraffin in the feed mixture.

In some embodiments, the amount of tungsten effective to isomerize n-heptane at a selectivity ratio of conversion to cracking for n-heptane of about 11 or greater may range from about 10 wt. % to about 16 wt. %, or about 11 wt. % to about 15 wt. %, or about 12 wt. % to about 14 wt. %, based on total mass of the mixed metal oxide. According to various embodiments, the amount of tungsten effective to isomerize n-heptane may range from about 13 wt. % to about 16 wt. %, based on total mass of the bifunctional mixed metal oxide catalyst. In at least one instance, the amount of tungsten effective to isomerize n-heptane at the foregoing selectivity ratio may be about 13 wt. %, based on total mass of the bifunctional mixed metal oxide.

Accordingly, in some embodiments, methods of the present disclosure may comprise: providing a bifunctional mixed metal oxide catalyst comprising a bifunctional mixed metal oxide impregnated with a noble metal; contacting the bifucntional mixed metal oxide catalyst under isomerization reaction conditions with a feed mixture comprising at least one C7+ normal paraffin; and obtaining one or more branched paraffins formed from the at least one C7+ normal paraffin under the isomerization reaction conditions. The bifunctional mixed metal oxide catalyst may comprise about 40 wt. % to about 70 wt. % zirconium and about 0.01 wt. % to about 5 wt. % variable oxidation state metal, each based on total mass of the bifunctional mixed metal oxide catalyst, and an amount of tungsten effective to isomerize n-heptane to one or more branched paraffins at about 70% to about 80% conversion under the isomerization reaction conditions with a selectivity ratio of conversion to cracking for n-heptane of about 11 or greater.

In at least one example, a bifunctional mixed metal oxide catalyst having a poorer selectivity ratio of conversion to cracking (e.g., less than about 11 at about 70% to about 80% conversion) may be utilized in combination with a bifunctional mixed metal oxide catalyst having a selectivity ratio of conversion to cracking of about 11 or greater at about 70% to about 80% conversion. For example, a bifunctional mixed metal oxide catalyst affording higher cracking selectivity may comprise about 16 wt. % tungsten or above, based on total mass of the bifunctional mixed metal oxide, in at least one embodiment of the present disclosure. Such bifunctional mixed metal oxide catalysts affording higher cracking selectivity may be utilized in a sequenced arrangement with a bifunctional mixed metal oxide catalysts affording lower cracking selectivity for contacting a feed mixture comprising C7+ normal paraffins, such as in a stacked bed arrangement, as discussed further below. Such bifunctional mixed metal oxide catalysts having higher cracking selectivity may also be utilized in various embodiments of the present disclosure without utilizing a catalyst exhibiting lower cracking selectivity, optionally in further combination with additional techniques for suppressing cracking as specified herein.

When preparing the bifunctional mixed metal oxide catalysts by co-precipitation and calcination, suitable sources of the Group 4 metal may include, for example, Group 4 salts (e.g., Zr salts) such as chlorides, oxychlorides, nitrates, acetates, alkoxides, and the like. The Group 4 salt may be water soluble and capable of forming a hydroxide precipitate upon addition of a base, such as ammonium hydroxide or alkylammonium hydroxide. Alkoxides may also be suitable Group 4 metal precursors upon hydrolysis with water to form the hydroxide precipitate. Suitable sources of the anion or oxyanion comprising the Group 6 metal, such as W, may include, for example, ammonium or sodium metatungstate, ammonium or sodium metamolybdate, tungsten chloride, molybdenum chloride, tungstic acid, molybdic acid, and any combination thereof.

Co-precipitation may take place in an alkaline solution, such as in the presence of ammonium hydroxide or an alkylammonium hydroxide. Alkali metal hydroxides may be used similarly as well. A hydroxide precipitate may be formed initially from the Group 4 salt and the anion or oxyanion comprising the Group 6 metal. The hydroxide precipitate may then be converted into a bifunctional mixed metal oxide through calcination. Calcination may take place in air at a temperature of about 600° C. to about 900° C. or about 650° C. to about 850° C., for example.

Once formed, the bifunctional mixed metal oxide may be directly impregnated with a Group 8-10 metal, such as a noble metal including Pt or Pd, or first extruded to form the bifunctional mixed metal oxide into a suitable shape, such as pellets, cylinders, lobed structures, and the like. Optionally, the bifunctional mixed metal oxide may be combined with a binder such as silica or alumina prior to performing extrusion. Following extrusion, calcination may again be conducted, such as at a temperature of about 600° C. or below.

Once a bifunctional mixed metal oxide has been formed, optionally after extrusion, the bifunctional mixed metal oxide may be impregnated with a metal suitable to promote isomerization in the presence of hydrogen gas, particularly through a dehydrogenation/hydrogenation mechanism. Group 8-10 metals may be effective in this regard. Impregnation may be conducted using incipient wetness or vacuum infiltration techniques, for example. According to various embodiments, the metal suitable to promote isomerization may be a noble metal, such as Pt or Pd. In the case of Pt, suitable sources for introducing this metal may include chloroplatinic acid, tetramineplatinum complexes, platinum chloride, and any combination thereof. After impregnation of the bifunctional mixed metal oxide has taken place, the metal suitable to promote isomerization may likewise be converted into an oxide form of the metal through calcination, such as at a temperature ranging from about 280° C. to about 360° C.

Impregnation of the bifunctional mixed metal oxide with the metal suitable to promote isomerization, such as a noble metal, may take place by an incipient wetness technique. Incipient wetness impregnation involves adding just enough liquid solution of a metal salt or other soluble metal form to fill the pores of the bifunctional mixed metal oxide completely without excess liquid being present. Vacuum infiltration may also be used similarly. Additional techniques suitable to introduce the metal suitable to promote isomerization may include, for example, co-impregnation, co-precipitation, physical admixing, and the like. In addition, the metal suitable to promote isomerization may be present upon a suitable support with which the mixed metal oxide is combined.

The bifunctional mixed metal oxide catalyst may have a total surface area of about 75 m2/g or above or about 85 m2/g or above. In more particular examples, the surface area of the bifunctional mixed metal oxide catalysts may range from about 60 m2/g to about 130 m2/g. Such measurements may be made by BET adsorption/desorption isotherms, particularly according to ISO 9277.

The bifunctional mixed metal oxide catalyst may have a tungsten surface density, measured as W atoms/nm2, ranging from about 2 to about 20, or about 2.2 to about 18, or about 2.4 to about 16, or about 2.4 to about 14, or about 2.6 to about 12, or about 2.8 to about 10, or about 3 to about 8, or about 4 to about 12, or about 5 to about 7. The tungsten (W) surface density can be calculated from (a) the measured W content (wt. %) obtained by X-ray fluorescence and (b) the measured surface area obtained by N2 BET.

The bifunctional mixed metal oxide catalyst may have an X-ray diffraction peak height ratio ranging from 0 to about 5 for monoclinic tungsten oxide (m-WO3) relative to monoclinic zirconium oxide (m-ZrO2). According to various embodiments, the X-ray diffraction peak height ratio may range from 0 to 3. The X-ray diffraction peaks are expressed as 2θ values and are determined using Cu K☐ radiation. The following approximate 2θ peak positions are characteristic: m-WO3=24.4° and m-ZrO2=28.4°. Tetragonal ZrO2 (t-ZrO2) may be found at an approximate 2θ peak position of 30.2°. A higher ratio of m-WO3 to m-ZrO2 may be associated with less W becoming active.

Up to about 50 wt. % binder may be present in combination with the bifunctional mixed metal oxide catalyst. The binder may comprise at least one substance selected from the group consisting of a W/Zr oxide, a W/Zr hydroxides, a W oxide, a W hydroxide, a Zr oxide, a Zr hydroxide, an Fe oxide, an Fe hydroxide, a Ti oxide, a Ti hydroxide, silica, silica alumina, a titania silica, an aluminum oxide, an aluminum hydroxide, and any combination thereof. Extruded samples may also be self-bound as well (i.e., no binder being present).

The isomerization processes disclosed herein may take place using any one or a mixture of C5+ normal paraffins. For example, isomerization may take place upon feed mixtures comprising one or more of C5 normal paraffins, C6 normal paraffins, C7 normal paraffins, C8 normal paraffins, C9 normal paraffins, C10 normal paraffins, C11 normal paraffins, C12 normal paraffins, or even higher normal paraffins. Mixtures of normal paraffins may also undergo isomerization in the disclosure herein, such as a feed mixture comprising C7+ normal paraffins and/or C8+ normal paraffins. In more specific examples, suitable feed mixtures may comprise a light naphtha comprising C5 normal paraffins, C6 normal paraffins, C7 normal paraffins, and optionally C8 normal paraffins. Heavy naphtha may be separated from light naphtha (e.g., by distillation) to produce a suitable feed mixture for undergoing isomerization in the disclosure herein. The heavy naphtha may comprise C8+ normal paraffins, optionally in combination with some C7 normal paraffins, and be further processed by catalytic reforming processes. Naphtha suitable for being separated into light naphtha and heavy naphtha for further upgrading according to the disclosure herein may have a boiling point range of about 96° F. to about 350° F. (about 35° C. to about 177° C.) and an average octane number of about 50 or lower.

FIG. 1 is a process flow diagram showing how a naphtha stream may be separated and processed according to the disclosure herein. Process 100 provides naphtha stream 102 to distillation unit 104. In illustrative embodiments, naphtha stream 102 may have a boiling point range about of about 96° F. (about 35° C.) to about 370° F. (about 188° C.). Distillation unit 104 may separate naphtha stream 102 into light naphtha fraction 106 and heavy naphtha fraction 110 at a suitable distillation cut point. In some embodiments, the distillation cut point may be selected such that the light naphtha fraction 106 contains C8− hydrocarbons (boiling point range of about 96° F. (about 35° C.) to about 210° F. (about 99° C.)) and heavy naphtha fraction 110 contains C8+ hydrocarbons (boiling point range of about 210° F. (about 99° C.) to about 370° F. (188° C.)). The distillation cut point may be about 210° F. in this example. It is to be appreciated that the distillation cut point is exemplary and may be higher or lower depending on application-specific needs. For example, a lower distillation cut point may exclude C8 normal paraffins from light naphtha fraction 106 and/or introduce C7 normal paraffins to heavy naphtha fraction 110. Following distillation, light naphtha fraction 106 may be processed under isomerization reaction conditions in isomerization unit 108, and heavy naphtha fraction 110 may be stored or further treated under catalytic reforming reaction conditions in reforming unit 112. Suitable catalytic reforming conditions will be familiar to persons having ordinary skill in the art. Isomerization unit 108 may include one or more reactors, where at least one reactor contains a bifunctional mixed metal oxide catalyst capable of promoting decreased cracking, as specified above, such as at least one tungstated zirconium oxide catalyst. Isomerization unit 108 may include one or more reactor beds comprising the bifunctional mixed metal oxide catalyst, including fixed beds, fluidized beds, ebullated beds, slurry beds, moving beds, and the like. In at least one embodiment, two tungstated zirconium oxide catalysts having different tungsten loadings may be utilized in a sequenced arrangement, as discussed further herein, such as a stacked bed configuration.

Optionally, unconverted normal alkanes obtained from isomerization unit 108 may be recycled thereto via recycle line 120. It is to be appreciated that the position of recycle line 120 is exemplary. For example, recycle line 120 may recycle unconverted normal paraffins to light naphtha fraction 106 instead of directly to isomerization unit 108. Recycling in this manner may increase the extent of normal paraffin conversion.

Raffinate obtained from reforming unit 112 may contain one or more C7– normal paraffins. Optionally, raffinate obtained from reforming unit 112 may be provided to light naphtha fraction 106 via raffinate recycle line 130. It is to be appreciated that the position of raffinate recycle line 130 is exemplary. For example, raffinate recycle line 130 may recycle normal paraffins in the raffinate directly to isomerization unit 108 instead of to light naphtha fraction 106.

Recycling the raffinate in this manner may afford increased conversion of the hydrocarbons originally present in naphtha stream 102.

Reforming unit 112 may operate in a temperature range of about 400° C. to about 520° C. and a pressure of about 100 psi to about 230 psi. In some embodiments, forming unit 112 may operate at a hydrogen:hydrocarbon molar ratio in a range of about 2.0 to about 4.5.

Accordingly, methods of the present disclosure may comprise separating a naphtha stream into a heavy naphtha fraction comprising C8+ normal paraffins and a light naphtha fraction comprising C7– or C8– normal paraffins, in which the light naphtha fraction is provided as the feed mixture. Optionally, unreacted normal paraffins may be extracted from a product mixture comprising one or more branched paraffins, and the unreacted normal paraffins may be provided directly or indirectly to the isomerization reaction conditions.

Methods of the present disclosure may further comprise exposing the heavy naphtha fraction to catalytic reforming conditions, and obtaining an aromatic-enriched hydrocarbon stream and a raffinate stream under the catalytic reforming conditions, in which the raffinate stream comprises one or more C7– hydrocarbons. Optionally, the raffinate stream may be provided directly or indirectly to the isomerization reaction conditions.

In addition to suppressing cracking of normal paraffins in the C7-C8 range for making gasoline hydrocarbons, the present disclosure may also facilitate decreased cracking when isomerizing larger paraffins in the C10-C30 range, for example. Hydrocarbons within this size range may be useful as diesel components or lubricants and may similarly benefit from isomerization to decrease melting points and alter pour points, cloud points or viscosity indices, as needed for particular end use applications. As such, the present disclosure offers broad applicability beyond just increasing the octane number of gasoline hydrocarbons.

The present disclosure also provides methods in which a feed mixture comprising C7+ normal paraffins is contacted sequentially with two different bifunctional mixed metal oxide catalysts for promoting paraffin isomerization. In particular, a bifunctional mixed metal oxide catalyst having decreased cracking selectivity may be contacted with a feed mixture downstream from a bifunctional mixed metal oxide catalyst having a higher cracking selectivity and a higher catalytic activity, such as in a stacked bed or similar sequenced arrangement in which the first bifunctional mixed metal oxide catalyst may contact the feed mixture before the second bifunctional mixed metal oxide catalyst. Contacting a feed mixed with the two bifunctional mixed metal oxide catalysts in this manner may afford higher conversion with lower cracking selectivity than would be possible for either bifunctional mixed metal oxide catalyst alone. Such methods of the present disclosure may comprise: providing a first bifunctional mixed metal oxide catalyst and a second bifunctional mixed metal oxide catalyst, each bifunctional mixed metal oxide catalyst being impregnated with a noble metal; wherein the second bifunctional mixed metal oxide catalyst comprises about 40 wt. % to about 70 wt. % zirconium and about 0.01 wt. % to about 5 wt. % variable oxidation state metal, each based on total mass of the mixed metal oxide, and an amount of tungsten effective to isomerize n-heptane to one or more branched paraffins at about 70% to about 80% conversion with a selectivity ratio of conversion to cracking for n-heptane of about 11 or greater, and the first bifunctional mixed metal oxide catalyst comprises about 40 wt. % to about 70 wt. % zirconium and about 0.01 wt. % to about 5 wt. % variable oxidation state metal, each based on total mass of the mixed metal oxide, and an amount of tungsten that is higher than that present in the second mixed metal oxide; sequentially contacting the first bifunctional mixed metal oxide catalyst and the second bifunctional mixed metal oxide catalyst, each impregnated with the noble metal, under isomerization reaction conditions with a feed mixture comprising at least one C7+ normal paraffin; and obtaining one or more branched paraffins formed from the at least one C7+ normal paraffin under the isomerization reaction conditions. Any of the mixed metal oxides disclosed herein as having increased cracking selectivity may be utilized as the second bifunctional mixed metal oxide catalyst. In a particular example, the first bifunctional mixed metal oxide catalyst may comprise about 16 wt. % tungsten or greater. Suitable isomerization reaction conditions for sequenced arrangement contacting may include those provided above. The sequenced arrangement may include a stacked bed configuration, or similar configuration in which the feed mixture contacts the first bifunctional mixed metal oxide catalyst before contacting the second bifunctional mixed metal oxide catalyst.

The bifunctional mixed metal oxide catalysts may be contacted with a feed mixture comprising one or more normal paraffins under isomerization reaction conditions effective to form one or more branched paraffins therefrom. Suitable isomerization reaction conditions in the disclosure herein may include contacting the feed mixture and the bifunctional mixed metal oxide catalyst with hydrogen gas. The bifunctional mixed metal oxide catalyst may be contacted with hydrogen gas before contact with the feed mixture takes place, such as at a temperature ranging from about 80° C. to about 300° C., or about 120° C. to about 220° C., or about 150° C. to about 220° C.

In some embodiments, contacting the bifunctional mixed metal oxide catalyst with the feed mixture may take place at a temperature ranging from about 80° C. to about 210° C. or a temperature ranging from about 150° C. to about 190° C. The mole ratio of hydrogen gas to feed mixture may range from about 5:1 to about 1:1, such as about 2:1 to about 1:1. The total pressure in a reactor in which the isomerization reaction is conducted may range from about 70 psig to about 600 psig, or about 100 psig to about 500 psig, or about 150 psig to about 350 psig. Hydrogen partial pressures may range from about 50 kPa to about 2000 kPa, for example.

The mole ratio of hydrogen gas to total hydrocarbons (or "H2:hydrocarbon ratio") under the isomerization reaction conditions may range from about 0.5 to about 4, inclusive of any value or subrange therebetween, such as about 0.5 to about 1, or about 1 to about 2, inclusive of any value or subrange therebetween.

The isomerization reaction conditions may further include a liquid hour space velocity (LHSV) of about 8 hr-1 or less, or about 7 hr-1 or less, or about 6 hr-1 or less, or about 5 hr-1 or less, or about 4 hr-1 or less, such as a LHSV ranging from about 0.5 hr-1 to about 8 hr-1, or about 1 hr-1 to about 5 hr-1, or about 2 hr-1 to about 5 hr-1, or about 1 hr-1 to about 2 hr-1, or about 0.5 hr-1 to about 2 hr-1.

The isomerization reaction conditions may be such that the isomerization reaction is carried out in the gas phase, a supercritical phase, or a liquid phase.

Cracking selectivity for C7+ normal paraffins may be significantly decreased by conducting isomerization in the presence of a suitable co-feed. In particular, by introducing a co-feed comprising one or more naphthenic compounds to a feed mixture comprising normal paraffins and/or monobranched paraffins, the incidence of cracking during paraffin isomerization may be lowered significantly, especially for C7+ normal and monobranched paraffins. The terms "naphthenic compounds" and "cycloalkanes" are synonymous with one another herein. Branched naphthenic compounds such as methylcyclopentane (MCP), methylcyclohexane (MCH), or any combination thereof may be especially effective for mitigating cracking when provided as a co-feed to a feed mixture comprising C7+ normal paraffins. For purposes of the present disclosure, tetraline is considered to be a napthenic compound and may be used alone or in combination with methylcyclopentane and/or methylcyclohexane in the various embodiments described herein.

One or more naphthenic compounds may be combined with a feed mixture comprising at least one C7+ normal paraffin to provide a co-feed that may experience a decreased extent of cracking. In non-limiting embodiments, the co-feed to which the one or more naphthenic compounds are added may comprise a light naphtha fraction comprising C5-C7 normal paraffins or C5-C8 normal paraffins, or the feed mixture may comprise C7 and/or C8 normal paraffins alone, optionally in further combination with other paraffins having a higher number of carbon atoms.

Advantageously, the presence of the naphthenic compounds is not believed to significantly impact the isomerization of lower normal paraffins (e.g., C5 and C6 normal paraffins), thereby allowing feed mixtures containing a range of normal and/or monobranched paraffins to undergo effective isomerization according to the disclosure herein. Not only may C7+ normal paraffins experience decreased cracking, but isomerization of C5 and C6 normal paraffins may surprisingly increase in the presence of C7+ normal paraffins and one or more naphthenic compounds. Further, the naphthenic compounds themselves may be isomerized to compounds that have higher octane number values than do normal paraffin compounds.

Without being bound by theory or mechanism, the naphthenic compounds are believed to function as a hydrogen donor under the isomerization reaction conditions. Branched naphthenic compounds may be particularly effective hydrogen donors due to the ease with which a hydrogen atom may be lost from their tertiary carbon centers. Extensive absorption of the naphthenic compounds may occur upon the catalyst surface under the isomerization reaction conditions. The donated hydrogen may cap a carbenium ion formed from linear or monobranched paraffins under isomerization reaction conditions, thereby suppressing cracking through β-scission. A tertiary carbenium ion may result upon the naphthenic compounds following hydrogen transfer. The tertiary carbenium ion upon the naphthenic compound may undergo dehydrogenation to form a cyclic olefin rather than undergoing β-scission to form a primary carbenium ion. Varying degrees of isomerization and/or ring expansion of the tertiary carbenium ion may also occur In particularly suitable examples, the one or more naphthenic compounds may comprise one or more branched naphthenic compounds. Particularly suitable branched naphthenic compounds for use in the disclosure herein may include methylcyclopentane (MCP), methylcyclohexane (MCH), or any combination thereof. These branched naphthenic compounds are readily obtained from various hydrocarbon resources. Other branched naphthenic compounds such as ethylcylopentane, propylcyclopentane, 1,1-dimethylcyclopentane, 1,1-dimethylcyclohexane, ethylcyclohexane, propylcyclohexane, and the like may also be suitable for use in the disclosure herein. In general, any naphthenic compound that may form a tertiary carbenium ion under isomerization reaction conditions may be used effectively in the disclosure herein. In some embodiments, the co-feed may consist essentially of methylcyclopentane, methylcyclohexane, or any combination thereof. In some embodiments, the co-feed may be a 1:1 mixture on a weight basis of methylcyclopentane and methylcyclohexane. In addition to one or more naphthenic compounds, the co-feed may comprise other H-atom donors such as alcohols, tetralin, or isobutene, for example. These alternative H-atom donors may be used in place of naphthenic compounds in some instances.

The combination of the feed mixture comprising at least one C7+ normal paraffin and the co-feed comprising one or more naphthenic compounds, such as one or more branched naphthenic compounds, may afford a combined feed that is contacted with the bifunctional mixed metal oxide catalyst. The combined feed may comprise about 10 wt. % or greater, or about 15 wt. % or greater, or about 20 wt. % or greater, or about 25 wt. % or greater, or about 30 wt. % or greater, or about 35 wt. % or greater, or about 40 wt. % or greater, or about 45 wt. % or greater, or about 50 wt. % or greater, or about 55 wt. % or greater, or about 60 wt. % or greater of the one or more naphthenic compounds, up to about 75 wt. % of the combined feed. In more particular examples, the combined feed may comprise about 5 wt. % to about 80 wt. %, or about 5 wt. % to about 60 wt. %, or about 10 wt. % to about 80 wt. %, or about 25 wt. % to about 75 wt. %, or about 40 wt. % to about 60 wt. %, or about 45 wt. % to about 55 wt. %, or about 25 wt. % to about 50 wt. %, or about 10 wt. % to about 50 wt. %, or about 10 wt. % to about 25 wt. % of the one or more naphthenic compounds. Thus, in particular examples, the feed mixture and the co-feed may be combined in any ration ranging from about 3:1 to 1:3, including about 1:1, on a weight basis (wt. %:wt. %).

In addition to the at least one C7+ normal paraffin, the feed mixture may further comprise one or more of at least one branched paraffin (e.g., a C5 monobranched paraffin, a C6 monobranched paraffin or a C7+ monobranched paraffin), a C5 normal paraffin, a C6 normal paraffin, or any combination thereof. Thus, particular feed mixtures suitable for use in the disclosure herein may comprise normal or monobranched C5 paraffins, normal or monobranched C6 paraffins, and normal or monobranched C7 paraffins. Optionally, at least some normal or monobranched C8 paraffins may be present in such feed mixtures as well. Other feed mixtures suitable for use in the disclosure herein may comprise at least one C10-C30 normal paraffin, optionally in combination with monobranched paraffins within this size range. Any of the foregoing may further comprise one or more aromatic compounds as well.

When isomerizing a feed mixture in the presence of a co-feed according to the disclosure herein, contacting may take place under isomerization reaction conditions that afford about 85% or less conversion of the one or more C7+ normal paraffins in the feed mixture. Alternately, the isomerization reaction conditions may afford about 80% or less conversion, or about 75% or less conversion, or about 70% or less conversion of the one or more C7+ normal paraffins in the feed mixture.

Accordingly, methods of the present disclosure may comprise: providing a feed mixture comprising at least one C7+ normal paraffin; combining a co-feed comprising one or more naphthenic compounds with the feed mixture; and contacting the feed mixture and the co-feed with a bifunctional mixed metal oxide catalyst under isomerization reaction conditions effective to form a product mixture comprising one or more branched paraffins formed from the at least one C7+ normal paraffin. A cracking selectivity of the at least one C7+ normal paraffin under the isomerization reaction conditions is about 15 wt. % or less, based on a total weight of the feed mixture. In non-limiting examples, the cracking selectivity for n-heptane may be about 10 wt. % or less or about 5 wt. % or less at about 80% or less conversion of the feed mixture, and/or the cracking selectivity for n-octane may be about 15 wt. % or less or about 10 wt. % or less at about 80% or less conversion of the feed mixture. In more specific examples, the feed mixture may undergo about 60% to about 80% conversion or about 70% to about 80% conversion to realize the foregoing values. In the case of C10-C30 normal paraffins, the cracking selectivity may be about 30 wt. % or less, based on total weight of the feed mixture, under the isomerization reaction conditions at about 80% or less conversion of the feed mixture, and such as about 10 wt. % or less, based on total weight of the feed mixture, under the isomerization reaction conditions at about 80% or less conversion of the feed mixture. Under the same conditions, the cracking selectivity for C8 normal paraffins to C7 normal paraffins (n-octane:n-heptane cracking selectivity ratio) may be about 5 or less or about 3 or less, such as about 2 to about 5, or about 3 to about 5.

Embodiments disclosed herein include:

A. Methods for isomerizing normal paraffins. The methods comprise: providing a feed mixture comprising at least C5-C7 normal paraffins; and contacting the feed mixture with a bifunctional mixed metal oxide catalyst under isomerization reaction conditions effective to form a product mixture comprising one or more branched paraffins formed from each of the C5-C7 normal paraffins.

B. Methods for isomerizing normal paraffins in the presence of naphthenic compounds. The methods comprise: providing a feed mixture comprising at least one C7+ normal paraffin; combining a co-feed comprising one or more naphthenic compounds with the feed mixture; and contacting the feed mixture and the co-feed with a bifunctional mixed metal oxide catalyst under isomerization reaction conditions effective to form a product mixture comprising one or more branched paraffins formed from the at least one C7+ normal paraffin; wherein a cracking selectivity of the at least one C7+ normal paraffin under the isomerization reaction conditions is about 15 wt. % or less, based on a total weight of the feed mixture.

C. Methods for isomerizing normal paraffins using a bifunctional mixed metal oxide having decreased cracking selectivity. The methods comprise: providing a bifunctional mixed metal oxide catalyst comprising a bifunctional mixed metal oxide impregnated with a noble metal; wherein the bifunctional mixed metal oxide comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater; contacting the bifunctional mixed metal oxide catalyst under the isomerization reaction conditions with a feed mixture comprising at least one C7+ normal paraffin; and obtaining one or more branched paraffins formed from the at least one C7+ normal paraffin under the isomerization reaction conditions.

D. Compositions for isomerizing normal paraffins at decreased cracking selectivity. The compositions comprise: a bifunctional mixed metal oxide impregnated with a noble metal, the bifunctional mixed metal oxide comprising tungsten, zirconium, and a variable oxidation state metal; wherein the bifunctional mixed metal oxide comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane under isomerization reaction conditions to one or more branched paraffins at about 70% to about 80% conversion with a selectivity ratio of conversion to cracking for n-heptane of about 11 or greater.

Embodiments A-D may have one or more of the following additional elements in any combination:

Element 1: wherein an extent of conversion of C5 and C6 normal paraffins under the isomerization reaction conditions in a presence of C7 normal paraffins is greater than an extent of conversion obtained when C5 or C6 normal paraffins are contacted with the bifunctional mixed metal oxide catalyst in an absence of C7 normal paraffins under the isomerization reaction conditions.

Element 2: wherein the feed mixture further comprises C8 normal paraffins.

Element 3: wherein the method further comprises separating a naphtha stream into a heavy naphtha fraction comprising C8+ hydrocarbons and a light naphtha fraction comprising C8− hydrocarbons, the light naphtha fraction being provided as the feed mixture.

Element 4: wherein the method further comprises separating a naphtha stream into a heavy naphtha fraction comprising C8+ hydrocarbons and a light naphtha fraction comprising C7− hydrocarbons, the light naphtha fraction being provided as the feed mixture.

Element 5: wherein the method further comprises exposing the heavy naphtha fraction to reforming reaction conditions; and obtaining an aromatic-enriched hydrocarbon stream and a raffinate stream under the reforming reaction conditions, the raffinate stream comprising one or more C7− hydrocarbons.

Element 6: wherein the method further comprises providing the raffinate stream to the isomerization reaction conditions.

Element 7: wherein the feed mixture further comprises one or more branched paraffins.

Element 8: wherein the feed mixture lacks normal paraffins larger than C8.

Element 8A: wherein the feed mixture comprises at least C5-C7 normal paraffins.

Element 9: wherein the method further comprises extracting unreacted normal paraffins from the product mixture; and providing the unreacted normal paraffins to the isomerization reaction conditions.

Element 10: wherein the method further comprises combining a co-feed comprising one or more naphthenic compounds with the feed mixture.

Element 10A: wherein the feed mixture and the co-feed are combined in a ratio of about 3:1 to about 1:3 on a weight basis.

Element 11: wherein the one or more naphthenic compounds comprise one or more branched naphthenic compounds.

Element 12: wherein the one or more naphthenic compounds comprise methylcyclopentane, methylcyclohexane, tetralin or any combination thereof.

Element 13: wherein the co-feed consists essentially of methylcyclopentane, methylcyclohexane, or any combination thereof.

Element 14: wherein the bifunctional mixed metal oxide catalyst comprises a bifunctional mixed metal oxide impregnated with a noble metal.

Element 14A: wherein the bifunctional mixed metal oxide catalyst is impregnated with about 0.01 wt. % to about 2 wt. % noble metal, based on total mass of the bifunctional mixed metal oxide.

Element 15: wherein the bifunctional mixed metal oxide catalyst comprises a tungstated zirconium oxide.

Element 16: wherein the noble metal comprises platinum.

Element 17: wherein the bifunctional mixed metal oxide catalyst further comprises a variable oxidation state metal selected from the group consisting of Fe, Mn, Co, Cu, Ce, and any combination thereof.

Element 17A: wherein the variable oxidation state metal comprises Fe.

Element 18: wherein the bifunctional mixed metal oxide catalyst comprises about 9 wt. % to about 20 wt. % tungsten, about 40 wt. % to about 70 wt. % Zr, and about 0.01 wt. % to about 2 wt. % variable oxidation state metal, each based on total mass of the bifunctional mixed metal oxide.

Element 19: wherein the isomerization reaction conditions comprise exposing the feed mixture to hydrogen gas at a temperature ranging from about 80° C. to about 220° C.

Element 19A: wherein the isomerization reaction conditions comprise exposing the feed mixture and the co-feed to hydrogen gas at a temperature ranging from about 80° C. to about 220° C.

Element 20: wherein the isomerization reaction conditions comprise a liquid hour space velocity (LHSV) of about 8 hr-1 or less.

Element 21: wherein the contacting takes place under isomerization reaction conditions that afford about 80% or less conversion of the one or more C7+ normal paraffins in the feed mixture.

Element 22: wherein the method further comprises activating the bifunctional mixed metal oxide catalyst by heating under hydrogen.

Element 23: wherein the selectivity ratio ranges from about 11 to about 14.

Element 24: wherein the amount of tungsten is effective to isomerize n-heptane at about 70% to about 80% conversion with a cracking yield for n-heptane of about 8 wt. % or less.

Element 25: wherein the amount of tungsten is effective to isomerize n-heptane at about 70% to about 80% conversion with a cracking yield for n-heptane of about 5 wt. % to about 7 wt. %.

Element 26: wherein the amount of tungsten effective to isomerize n-heptane ranges from about 10 wt. % to about 16 wt. %, based on total mass of the bifunctional mixed metal oxide.

Element 27: wherein the amount of tungsten effective to isomerize n-heptane ranges from about 13 wt. % to about 16 wt. %, based on total mass of the bifunctional mixed metal oxide.

Element 28: wherein the amount of tungsten effective to isomerize n-heptane is about 13 wt. %, based on total mass of the mixed metal oxide.

Element 29: wherein the bifunctional mixed metal oxide catalyst is provided as a second bifunctional mixed metal oxide catalyst, the method further comprising: providing a first bifunctional mixed metal oxide catalyst comprising a first bifunctional mixed metal oxide impregnated with noble metal, the first bifunctional mixed metal oxide catalyst comprising about 40 wt. % to about 70 wt. % zirconium and about 0.01 wt. % to about 5 wt. % variable oxidation state metal, each based on total mass of the mixed metal oxide, and an amount of tungsten that is higher than that present in the second bifunctional mixed metal oxide catalyst; and sequentially contacting the first bifunctional mixed metal oxide catalyst and the second bifunctional mixed metal oxide catalyst under the isomerization reaction conditions with the feed mixture comprising at least one C7+ normal paraffin.

Element 30: wherein the feed mixture contacts the first bifunctional mixed metal oxide catalyst before contacting the second bifunctional mixed metal oxide catalyst.

Element 31: wherein the first bifunctional mixed metal oxide catalyst and the second bifunctional mixed metal oxide catalyst are arranged in a stacked bed configuration.

By way of non-limiting example, illustrative combinations applicable to A-D include, but are not limited to, 1 and 2; 1-3; 1, 2 and 4; 1, and 3 or 4; 1 and 5; 1, 5 and 6; 1 and 7; 1, 2 and 7; 1 and 8; 1, 2 and 8; 1, 2, 7 and 8; 1 and 8A; 1, 7 and 8A; 1 and 9; 1 and 10; 1, 10 and 10A; 1, 10 and 11; 1, 10, 11 and 12; 1, 10 and 12; 1, 10 and 13; 1, and 14 or 14A; 1 and 15; 1, 15, and 17 or 17A; 1, and 17 or 17A; 1 and 18; 1, and 19 or 19A; 1, and 20 or 21; 2 and 3; 2 and 4; 2 and 5; 2 and 6; 2 and 7; 2 and 8; 2, 7 and 8; 2 and 8A; 2, 7 and 8A; 2 and 9; 2 and 10; 2, 10 and 10A; 2, 10 and 11; 2, 10, 11 and 12; 2, 10 and 13; 2, and 14 or 14A; 2 and 15; 2, 15 and 17 or 17A; 2, and 17 or 17A; 2 and 18; 2, and 20 or 21; 3 or 4, and 5; 3 or 4, and 6; 3 or 4, and 7; 3 or 4, and 8; 3 or 4, 7 and 8; 3 or 4, and 8A; 3 or 4, 7 and 8A; 3 or 4, and 9; 3 or 4, and 10; 3 or 4, 10 and 10A; 3 or 4, 10 and 11; 3 or 4, 10, 11 and 12; 3 or 4, 10 and 13; 3 or 4, and 14 or 14A; 3 or 4, and 15; 3 or 4, 15 and 17 or 17A; 3 or 4, and 17 or 17A; 3 or 4, and 18; 3 or 4, and 20 or 21; 7 and 8; 7 and 8A; 7 and 9; 7 and 10; 7, 10 and 10A; 7, 10 and 11; 7, 10, 11 and 12; 7, 10 and 13; 7, and 14 or 14A; 7, and 15; 7, 15 and 17 or 17A; 7, and 17 or 17A; 7, and 18; 7, and 20 or 21; 8 or 8A, and 9; 8 or 8A, and 10; 8 or 8A, 10 and 10A; 8 or 8A, 10 and 11; 8 or 8A, 10, 11 and 12; 8 or 8A, 10 and 13; 8 or 8A, and 14 or 14A; 8 or 8A, and 15; 8 or 8A, 15 and 17 or 17A; 8 or 8A, and 17 or 17A; 8 or 8A, and 18; 8 or 8A, and 20 or 21; 9 and 10; 9, 10 and 10A; 9, 10 and 11; 9, 10, 11 and 12; 9, 10 and 13; 9, and 14 or 14A; 9 and 15; 9, 15 and 17 or 17A; 9, and 17 or 17A; 9, and 18; 9, and 20 or 21; 10 or 10A, and 11; 10 or 10A, 11 and 12; 10 or 10A, and 13; 10 or 10A, and 14 or 14A; 10 or 10A, and 15; 10 or 10A, 15 and 17 or 17A; 10 or 10A, and 17 or 17A; 10 or 10A, and 18; 10 or 10A, and 20 or 21; 14 or 14A, and 15; 14 or 14A, 15, and 17 or 17A; 14 or 14A, and 17 or 17A; 14 or 14A, and 18; 14 or 14A, and 19 or 19A; 14 or 14A, and 20 or 21; 15 and 16; 15, and 17 or 17A; 15, 16, and 17 or 17A; 15 and 18; 15, and 19 or 19A; 15, and 20 or 21; 17 and 18; 17, and 19 or 19A; 17; and 20 or 21; 18, and 19 or 19A; and 18, and 20 or 21. With respect to C, any one or more of 1-21 may be combined with one or more of 23-30. Additional exemplary combinations applicable to C include, but are not limited to, 23, and 24 or 25; 23, and 26, 27 or 28; 23 and 29; 23, 29, and 30 or 31; 24 or 25, and 26, 27 or 28; 24 or 25, and 29; 24 or 25, 29, and 30 or 31; 26, 27 or 28, and 29; and 26, 27 or 28, 29, and 30 or 31.

Additional embodiments include:

Clause 1. A method comprising:
providing a feed mixture comprising at least C5-C7 normal paraffins; and
contacting the feed mixture with a bifunctional mixed metal oxide catalyst under isomerization reaction conditions effective to form a product mixture comprising one or more branched paraffins formed from each of the C5-C7 normal paraffins.

Clause 2. The method of clause 1, wherein an extent of conversion of $C_5$ and $C_6$ normal paraffins under the isomerization reaction conditions in a presence of $C_7$ normal paraffins is greater than an extent of conversion obtained when $C_5$ or $C_6$ normal paraffins are contacted with the bifunctional mixed metal oxide catalyst in an absence of $C_7$ normal paraffins under the isomerization reaction conditions.

Clause 3. The method of clause 1 or clause 2, wherein the feed mixture further comprises $C_8$ normal paraffins.

Clause 4. The method of clause 3, further comprising:
separating a naphtha stream into a heavy naphtha fraction comprising $C_{8+}$ hydrocarbons and a light naphtha fraction comprising $C_{8-}$ hydrocarbons, the light naphtha fraction being provided as the feed mixture.

Clause 5. The method of clause 1 or clause 2, further comprising:
separating a naphtha stream into a heavy naphtha fraction comprising $C_{8+}$ hydrocarbons and a light naphtha fraction comprising $C_{7-}$ hydrocarbons, the light naphtha fraction being provided as the feed mixture.

Clause 6. The method of clause 4 or clause 5, further comprising:
exposing the heavy naphtha fraction to reforming reaction conditions; and
obtaining an aromatic-enriched hydrocarbon stream and a raffinate stream under the reforming reaction conditions, the raffinate stream comprising one or more $C_{7-}$ hydrocarbons.

Clause 7. The method of clause 6, further comprising:
providing the raffinate stream to the isomerization reaction conditions.

Clause 8. The method of any one of clauses 1-7, wherein the feed mixture further comprises one or more branched paraffins.

Clause 9. The method of any one of clauses 1-8, wherein the feed mixture lacks normal paraffins larger than $C_8$.

Clause 10. The method of any one of clauses 1-9, further comprising:
extracting unreacted normal paraffins from the product mixture; and
providing the unreacted normal paraffins to the isomerization reaction conditions.

Clause 11. The method of any one of clauses 1-10, further comprising:
combining a co-feed comprising one or more naphthenic compounds with the feed mixture.

Clause 12. The method of clause 11, wherein the one or more naphthenic compounds comprise one or more branched naphthenic compounds.

Clause 13. The method of clause 11 or clause 12, wherein the one or more naphthenic compounds comprise methylcyclopentane, methylcyclohexane, tetralin or any combination thereof.

Clause 14. The method of any one of clauses 11-13, wherein the co-feed consists essentially of methylcyclopentane, methylcyclohexane, or any combination thereof.

Clause 15. The method of any one of clauses 1-14, wherein the bifunctional mixed metal oxide catalyst comprises a bifunctional mixed metal oxide impregnated with a noble metal.

Clause 16. The method of clause 15, wherein the bifunctional mixed metal oxide catalyst comprises a tungstated zirconium oxide.

Clause 17. The method of clause 15 or clause 16, wherein the noble metal comprises platinum.

Clause 18. The method of any one of clauses 15-17, wherein the bifunctional mixed metal oxide catalyst further comprises a variable oxidation state metal selected from the group consisting of Fe, Mn, Co, Cu, Ce, and any combination thereof.

Clause 19. The method of any one of clauses 15-18, wherein the bifunctional mixed metal oxide catalyst comprises about 9 wt. % to about 20 wt. % tungsten, about 40 wt. % to about 70 wt. % Zr, and about 0.01 wt. % to about 2 wt. % variable oxidation state metal, each based on total mass of the bifunctional mixed metal oxide.

Clause 20. The method of any one of clauses 1-19, wherein the isomerization reaction conditions comprise exposing the feed mixture to hydrogen gas at a temperature ranging from about 80° C. to about 220° C.

Clause 21. The method of any one of clauses 1-20, wherein the isomerization reaction conditions comprise a liquid hour space velocity (LHSV) of about 8 $hr^{-1}$ or less.

Clause 22. A method comprising:
providing a feed mixture comprising at least one $C_{7+}$ normal paraffin;
combining a co-feed comprising one or more naphthenic compounds with the feed mixture; and
contacting the feed mixture and the co-feed with a bifunctional mixed metal oxide catalyst under isomerization reaction conditions effective to form a product mixture comprising one or more branched paraffins formed from the at least one $C_{7+}$ normal paraffin; wherein a cracking selectivity of the at least one $C_{7+}$ normal paraffin under the isomerization reaction conditions is about 15 wt. % or less, based on a total weight of the feed mixture.

Clause 23. The method of clause 22, wherein the one or more naphthenic compounds comprise one or more branched naphthenic compounds.

Clause 24. The method of clause 22 or clause 23, wherein the one or more naphthenic compounds comprise methylcyclopentane, methylcyclohexane, tetralin, or any combination thereof.

Clause 25. The method of any one of clauses 22-24, wherein the co-feed consists essentially of methylcyclopentane, methylcyclohexane, or any combination thereof.

Clause 26. The method of any one of clauses 22-25, wherein the contacting takes place under isomerization reaction conditions that afford about 80% or less conversion of the one or more $C_{7+}$ normal paraffins in the feed mixture.

Clause 27. The method of any one of clauses 22-26, wherein the bifunctional mixed metal oxide catalyst comprises a bifunctional mixed metal oxide impregnated with a noble metal.

Clause 28. The method of clause 27, wherein the bifunctional mixed metal oxide catalyst comprises a tungstated zirconium oxide.

Clause 29. The method of clause 27 or clause 28, wherein the noble metal comprises platinum.

Clause 30. The method of any one of clauses 27-29, wherein the bifunctional mixed metal oxide catalyst further comprises a variable oxidation state metal selected from the group consisting of Fe, Mn, Co, Cu, Ce, and any combination thereof.

Clause 31. The method of any one of clauses 27-30, wherein the bifunctional mixed metal oxide catalyst comprises about 9 wt. % to about 20 wt. % tungsten, about 40 wt. % to 70 wt. % Zr, and about 0.01 wt. % to 2 wt. % variable oxidation state metal, each based on total mass of the bifunctional mixed metal oxide.

Clause 32. The method of any one of clauses 22-31, wherein the feed mixture and the co-feed are combined in a ratio of about 3:1 to about 1:3 on a weight basis.

Clause 33. The method of any one of clauses 22-32, wherein the isomerization reaction conditions comprise exposing the feed mixture and the co-feed to hydrogen gas at a temperature ranging from about 80° C. to about 220° C.

Clause 34. The method of any one of clauses 22-33, wherein the isomerization reaction conditions comprise a liquid hour space velocity (LHSV) of about 8 hr$^{-1}$ or less.

Clause 35. The method of any one of clauses 22-34, further comprising:
activating the bifunctional mixed metal oxide catalyst by heating under hydrogen.

Clause 36. The method of any one of clauses 22-35, wherein the feed mixture lacks normal paraffins larger than $C_8$.

Clause 37. The method of any one of clauses 22-36, wherein the feed mixture comprises at least $C_5$-$C_7$ normal paraffins.

Clause 38. The method of any one of clauses 22-37, wherein the feed mixture further comprises one or more branched paraffins.

Clause 39. A method comprising:
providing a bifunctional mixed metal oxide catalyst comprising a bifunctional mixed metal oxide impregnated with a noble metal; wherein the bifunctional mixed metal oxide catalyst comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater;
contacting the bifunctional mixed metal oxide catalyst under the isomerization reaction conditions with a feed mixture comprising at least one $C_{7+}$ normal paraffin; and
obtaining one or more branched paraffins formed from the at least one $C_{7+}$ normal paraffin under the isomerization reaction conditions.

Clause 40. The method of clause 39, wherein the selectivity ratio ranges from about 11 to about 14.

Clause 41. The method of clause 39 or clause 40, wherein the amount of tungsten is effective to isomerize n-heptane at about 70% to about 80% conversion with a cracking yield for n-heptane of about 8 wt. % or less.

Clause 42. The method of clause 41, wherein the amount of tungsten is effective to isomerize n-heptane at about 70% to about 80% conversion with a cracking yield for n-heptane of about 5 wt. % to about 7 wt. %.

Clause 43. The method of clause 39 or clause 40, wherein the amount of tungsten effective to isomerize n-heptane ranges from about 10 wt. % to about 16 wt. %, based on total mass of the bifunctional mixed metal oxide.

Clause 44. The method of clause 43, wherein the amount of tungsten effective to isomerize n-heptane ranges from about 13 wt. % to about 16 wt. %, based on total mass of the bifunctional mixed metal oxide.

Clause 45. The method of clause 43, wherein the amount of tungsten effective to isomerize n-heptane is about 13 wt. %, based on total mass of the mixed metal oxide.

Clause 46. The method of any one of clauses 39-45, wherein the noble metal comprises platinum.

Clause 47. The method of any one of clauses 39-46, wherein the bifunctional mixed metal oxide catalyst is impregnated with about 0.01 wt. % to about 2 wt. % noble metal, based on total mass of the mixed metal oxide.

Clause 48. The method of any one of clauses 39-47, wherein the variable oxidation state metal comprises Fe.

Clause 49. The method of any one of clauses 39-48, wherein the bifunctional mixed metal oxide catalyst is provided as a second bifunctional mixed metal oxide catalyst, the method further comprising:
providing a first bifunctional mixed metal oxide catalyst comprising a first bifunctional mixed metal oxide impregnated with noble metal, the first bifunctional mixed metal oxide catalyst comprising about 40 wt. % to about 70 wt. % zirconium and about 0.01 wt. % to about 5 wt. % variable oxidation state metal, each based on total mass of the mixed metal oxide, and an amount of tungsten that is higher than that present in the second bifunctional mixed metal oxide catalyst; and
sequentially contacting the first bifunctional mixed metal oxide catalyst and the second bifunctional mixed metal oxide catalyst under the isomerization reaction conditions with the feed mixture comprising at least one $C_{7+}$ normal paraffin.

Clause 50. The method of clause 49, wherein the feed mixture contacts the first bifunctional mixed metal oxide catalyst before contacting the second bifunctional mixed metal oxide catalyst.

Claus 51. The method of clause 49 or clause 50, wherein the first bifunctional mixed metal oxide catalyst and the second bifunctional mixed metal oxide catalyst are arranged in a stacked bed configuration.

Clause 52. The method of any one of clauses 39-51, wherein the feed mixture lacks normal paraffins larger than $C_8$.

Clause 53. The method of any one of clauses 39-52, wherein the feed mixture comprises at least $C_5$-$C_7$ normal paraffins.

Clause 54. The method of any one of clauses 39-53, wherein the feed mixture further comprises one or more branched paraffins.

Clause 55. A composition comprising:
a bifunctional mixed metal oxide impregnated with a noble metal, the bifunctional mixed metal oxide comprising tungsten, zirconium, and a variable oxidation state metal;
wherein the bifunctional mixed metal oxide comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane under isomerization reaction conditions to one or more branched paraffins at about 70% to about 80% conversion with a selectivity ratio of conversion to cracking for n-heptane of about 11 or greater.

Clause 56. The composition of clause 55, wherein the selectivity ratio ranges from about 11 to about 14.

Clause 57. The composition of clause 55 or clause 56, wherein the amount of tungsten is effective to isomerize n-heptane at about 70% to about 80% conversion with a cracking yield for n-heptane of about 8 wt. % or less.

Clause 58. The composition of clause 55 or clause 56, wherein the amount of tungsten is effective to isomerize n-heptane at about 70% to about 80% conversion with a cracking yield of about 5 wt. % to about 7 wt. %.

Clause 59. The composition of clause 55 or clause 56, wherein the amount of tungsten effective to isomerize n-heptane ranges from about 10 wt. % to about 16 wt. %, based on total mass of the bifunctional mixed metal oxide.

Clause 60. The composition of clause 59, wherein the amount of tungsten effective to isomerize n-heptane ranges from about 13 wt. % to about 16 wt. %, based on total mass of the bifunctional mixed metal oxide.

Clause 61. The composition of clause 59, wherein the amount of tungsten effective to isomerize n-heptane is about 13 wt. %, based on total mass of the bifunctional mixed metal oxide.

Clause 62. The composition of any one of clauses 55-61, wherein the noble metal comprises platinum.

Clause 63. The composition of any one of clauses 55-62, wherein the bifunctional mixed metal oxide is impregnated with about 0.01 wt. % to about 2 wt. % noble metal, based on total mass of the bifunctional mixed metal oxide.

Clause 64. The composition of any one of clauses 55-63, wherein the variable oxidation state metal comprises Fe.

Still additional embodiments include:

Clause 1. A method comprising:
providing a feed mixture comprising at least $C_5$-$C_7$ normal paraffins; and
contacting the feed mixture with a bifunctional mixed metal oxide catalyst under isomerization reaction conditions effective to form a product mixture comprising one or more branched paraffins formed from each of the $C_5$-$C_7$ normal paraffins.

Clause 2. The method of clause 1, wherein the feed mixture further comprises $C_8$ normal paraffins.

Clause 3. The method of clause 2, further comprising:
separating a naphtha stream into a heavy naphtha fraction comprising $C_{8+}$ hydrocarbons and a light naphtha fraction comprising $C_{8-}$ hydrocarbons, the light naphtha fraction being provided as the feed mixture.

Clause 4. The method of clause 1, further comprising:
separating a naphtha stream into a heavy naphtha fraction comprising $C_{8+}$ hydrocarbons and a light naphtha fraction comprising $C_{7-}$ hydrocarbons, the light naphtha fraction being provided as the feed mixture.

Clause 5. The method of any one of clauses 1-4, wherein the feed mixture further comprises one or more branched paraffins.

Clause 6. The method of any one of clauses 1-5, wherein the feed mixture lacks normal paraffins larger than $C_8$.

Clause 7. The method of any one of clauses 1-6, further comprising:
combining a co-feed comprising one or more naphthenic compounds with the feed mixture.

Clause 8. The method of clause 7, wherein the one or more naphthenic compounds comprise one or more branched naphthenic compounds.

Clause 9. The method of clause 7 or clause 8, wherein the one or more naphthenic compounds comprise methylcyclopentane, methylcyclohexane, tetralin or any combination thereof.

Clause 10. The method of any one of clauses 7-9, wherein the co-feed consists essentially of methylcyclopentane, methylcyclohexane, or any combination thereof.

Clause 11. The method of any one of clauses 1-10, wherein the bifunctional mixed metal oxide catalyst comprises a bifunctional mixed metal oxide impregnated with a noble metal.

Clause 12. The method of clause 11, wherein the bifunctional mixed metal oxide catalyst comprises a tungstated zirconium oxide.

Clause 13. The method of clause 11 or clause 12, wherein the bifunctional mixed metal oxide catalyst further comprises a variable oxidation state metal selected from the group consisting of Fe, Mn, Co, Cu, Ce, and any combination thereof.

Clause 14. The method of any one of clauses 11-13, wherein the bifunctional mixed metal oxide catalyst comprises about 9 wt. % to about 20 wt. % tungsten, about 40 wt. % to about 70 wt. % Zr, and about 0.01 wt. % to about 2 wt. % variable oxidation state metal, each based on total mass of the bifunctional mixed metal oxide.

Clause 15. A method comprising:
providing a feed mixture comprising at least one $C_{7+}$ normal paraffin;
combining a co-feed comprising one or more naphthenic compounds with the feed mixture; and
contacting the feed mixture and the co-feed with a bifunctional mixed metal oxide catalyst under isomerization reaction conditions effective to form a product mixture comprising one or more branched paraffins formed from the at least one $C_{7+}$ normal paraffin; wherein a cracking selectivity of the at least one $C_{7+}$ normal paraffin under the isomerization reaction conditions is about 15 wt. % or less, based on a total weight of the feed mixture.

Clause 16. The method of clause 15, wherein the one or more naphthenic compounds comprise one or more branched naphthenic compounds.

Clause 17. The method of clause 15 or clause 16, wherein the one or more naphthenic compounds comprise methylcyclopentane, methylcyclohexane, tetralin, or any combination thereof.

Clause 18. The method of any one of clauses 15-17, wherein the co-feed consists essentially of methylcyclopentane, methylcyclohexane, or any combination thereof.

Clause 19. The method of any one of clauses 15-18, wherein the contacting takes place under isomerization reaction conditions that afford about 80% or less conversion of the one or more $C_{7+}$ normal paraffins in the feed mixture.

Clause 20. The method of any one of clauses 15-19, wherein the bifunctional mixed metal oxide catalyst comprises a bifunctional mixed metal oxide impregnated with a noble metal.

Clause 21. The method of clause 20, wherein the bifunctional mixed metal oxide catalyst comprises a tungstated zirconium oxide.

Clause 22. The method of clause 20 or 21, wherein the bifunctional mixed metal oxide catalyst further comprises a variable oxidation state metal selected from the group consisting of Fe, Mn, Co, Cu, Ce, and any combination thereof.

Clause 23. The method of any one of clauses 20-22, wherein the bifunctional mixed metal oxide catalyst comprises about 9 wt. % to about 20 wt. % tungsten, about 40 wt. % to 70 wt. % Zr, and about 0.01 wt. % to 2 wt. % variable oxidation state metal, each based on total mass of the bifunctional mixed metal oxide.

Clause 24. The method of any one of clauses 15-23, wherein the feed mixture lacks normal paraffins larger than $C_8$.

Clause 25. The method of any one of clauses 15-24, wherein the feed mixture comprises at least $C_5$-$C_7$ normal paraffins.

Clause 26. The method of any one of clauses 15-25, wherein the feed mixture further comprises one or more branched paraffins.

Clause 27. A method comprising:
providing a bifunctional mixed metal oxide catalyst comprising a bifunctional mixed metal oxide impregnated with a noble metal; wherein the bifunctional mixed metal oxide catalyst comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater;
contacting the bifunctional mixed metal oxide catalyst under the isomerization reaction conditions with a feed mixture comprising at least one $C_{7+}$ normal paraffin; and
obtaining one or more branched paraffins formed from the at least one $C_{7+}$ normal paraffin under the isomerization reaction conditions.

Clause 28. The method of clause 27, wherein the selectivity ratio ranges from about 11 to about 14.

Clause 29. The method of clause 27 or clause 28, wherein the amount of tungsten is effective to isomerize n-heptane at about 70% to about 80% conversion with a cracking yield for n-heptane of about 8 wt. % or less.

Clause 30. The method of clause 27, wherein the amount of tungsten effective to isomerize n-heptane ranges from about 13 wt. % to about 16 wt. %, based on total mass of the bifunctional mixed metal oxide.

Clause 31. The method of any one of clauses 27-30, wherein the variable oxidation state metal comprises Fe.

Clause 32. The method of any one of clauses 27-31, wherein the bifunctional mixed metal oxide catalyst is provided as a second bifunctional mixed metal oxide catalyst, the method further comprising:
providing a first bifunctional mixed metal oxide catalyst comprising a first bifunctional mixed metal oxide impregnated with noble metal, the first bifunctional mixed metal oxide catalyst comprising about 40 wt. % to about 70 wt. % zirconium and about 0.01 wt. % to about 5 wt. % variable oxidation state metal, each based on total mass of the mixed metal oxide, and an amount of tungsten that is higher than that present in the second bifunctional mixed metal oxide catalyst; and
sequentially contacting the first bifunctional mixed metal oxide catalyst and the second bifunctional mixed metal oxide catalyst under the isomerization reaction conditions with the feed mixture comprising at least one $C_{7+}$ normal paraffin.

Clause 33. The method of any one of clauses 27-32, wherein the feed mixture lacks normal paraffins larger than $C_8$.

Clause 34. The method of any one of clauses 27-33, wherein the feed mixture comprises at least $C_5$-$C_7$ normal paraffins.

Clause 35. The method of any one of clauses 27-34, wherein the feed mixture further comprises one or more branched paraffins.

Clause 36. A composition comprising:
a bifunctional mixed metal oxide impregnated with a noble metal, the bifunctional mixed metal oxide comprising tungsten, zirconium, and a variable oxidation state metal;
wherein the bifunctional mixed metal oxide comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane under isomerization reaction conditions to one or more branched paraffins at about 70% to about 80% conversion with a selectivity ratio of conversion to cracking for n-heptane of about 11 or greater.

Clause 37. The composition of clause 36, wherein the selectivity ratio ranges from about 11 to about 14.

Clause 38. The composition of clause 36 or clause 37, wherein the amount of tungsten is effective to isomerize n-heptane at about 70% to about 80% conversion with a cracking yield for n-heptane of about 8 wt. % or less.

Clause 39. The composition of clause 36 or clause 37, wherein the amount of tungsten effective to isomerize n-heptane ranges from about 13 wt. % to about 16 wt. %, based on total mass of the bifunctional mixed metal oxide.

Clause 40. The composition of any one of clauses 36-39, wherein the variable oxidation state metal comprises Fe.

To facilitate a better understanding of the present disclosure, the following examples of preferred or representative embodiments are given. In no way should the following examples be read to limit, or to define, the scope of the invention.

EXAMPLES

Catalyst synthesis. Tungstated zirconium oxide catalyst was prepared by co-precipitation in the following manner and loaded with 0.5 wt. % Pt thereafter. Solution A was prepared by dissolving 179.4 g of ammonium metatungstate (65%) and 37.26 g of ammonium hydroxide in 250 g of deionized water and heating to 60° C. with stirring. Solution B was prepared by dissolving 345 g zirconyl chloride (98%) and 5.25 g iron (II) sulfate heptahydrate in 250 g deionized water and heating to 60° C. with stirring.

A Syrris Atlas HD reactor was charged with 525 g of deionized water, and the pH was adjusted to 9.0 through addition of approximately 1 mL of ammonium hydroxide. This solution was then heated to 40° C. while stirring at 300 rpm. Solutions A and B were then fed into the reactor at a rate of 10 mL/min over 50 minutes using a dual dosing syringe pump. During this time, the stirring rate was ramped to 600 rpm to account for increased viscosity within the reaction mixture. After Solutions A and B were completely added, the stirring rate was adjusted to 500-525 rpm, and the reaction mixture was allowed to stir for an additional hour at 40° C.

The reaction mixture (both liquids and solids) was then transferred to a polypropylene bottle and inserted in a steam box maintained at 100° C. for 72 hours. Afterward, the reaction mixture was removed from the steam box and filtered while hot. The filter cake was slurried in 2000 mL of deionized water and filtered again. This operation was then repeated twice more. The resulting solids were air dried and then further dried in an oven held at 85° C. for 4 hours or more.

The dried solids were then combined with 1.0 N ammonium nitrate (pH>4.0, 10 mL/g of solids, pH adjusted with ammonium hydroxide). The resulting mixture was stirred for 1 hour and then filtered. This operation was repeated twice more. The solids were then slurried in deionized water (10 mL/g of solids), and the slurry was stirred for one hour and filtered. The resulting solids were air dried and then further dried in an oven held at 85° C. for 4 hours or more.

The resulting powder was laid in a thin bed and calcined in an oven ramped to 750° C. at a rate of 3° C./min under 5000 sccm air. The powder was held at 750° C. for three hours after reaching this temperature. The average peak height ratio from powder X-ray diffraction of monoclinic tungsten oxide:monoclinic zirconium oxide was 0.90 after calcination at 750° C.

After calcining, 10 g of the material was ground to a fine powder in a mortar and pestle or tube mill. The ground powder was then combined with 1 g vegetable oil and mixed until uniform, followed by 2.47 g of deionized water, and further mixed until uniform. The final mixture was added to an extruder utilizing a carver press, and extrusion was conducted with a 1/16" quadrulobe die. After drying overnight at 250° F., the extrudates were washed with 1.0 N ammonium hydroxide for 1 hour. The washing operation was repeated three additional times. Thereafter, the extrudates were washed in a continuous water flow for 1 hour, followed by drying overnight at 250° F. in an oven.

The extrudates were then impregnated with Pt using chloroplatinic acid as a Pt source. An 8 wt. % chloroplatinic acid solution in water was first prepared (3.8 wt. % Pt). This solution was then diluted to a volume sufficient to provide 0.5 wt. % Pt once loaded upon the extrudates. The extrudates were placed within a rota-cone operated at a spin rate of 30 rpm. The chloroplatinic acid solution was then added dropwise to the rota-cone, and rotation was continued for 20 minutes more after addition of the chloroplatinic acid solution was complete. Thereafter, the extrudates were dried in an oven for 2 hours at 250° F. Finally, the Pt-loaded extrudates were calcined in a muffle pot ramped to 572° F. at a ramp rate of 3° F./min, followed by a hold for 3 hours at the final temperature in 5 v/v air (volumes of extrudates per volume of air). The Pt-loaded extrudates were further activated under hydrogen prior to promoting isomerization, as described further below.

Isomerization Reactor, Catalyst Reduction and Reaction Conditions. A stainless steel tube reactor (3/8" OD×20.5"×0.035" wall thickness) was used to conduct the isomerization reactions. An 8" piece of stainless steel tubing (1/4" OD×0.018 id×0.035" wall thickness) was utilized at the bottom of the larger stainless steel tube as a spacer to position and support the catalyst in an isothermal zone once the reactor was housed in a furnace. The spacer was placed over a 1/8" stainless steel thermowell having a movable thermocouple positioned in the catalyst bed. Catalyst was held within the reactor using a 1/4" piece of glass wool placed at the top of the spacer.

The catalyst extrudates were sized to 20/40 mesh or cut to a 1:1 length:diameter ratio and mixed with 20/40 quartz chips when loaded into the reactor. The loading volume of catalyst extrudates and quartz chips was 5 mL (bed height of approximately 10 cm). The remaining void space at the top of the reactor was filled with quartz chips, and a 1/4" piece of glass wool was placed to separate the quartz chips from the catalyst bed. The reactor was then installed in a furnace in a pre-defined isothermal zone. Leak testing of the reactor was conducted at 1000 psig.

For isomerization reactions conducted in Examples 1-5 and 7, the catalyst was activated by heating the reactor from 25° C. to 240° C. with $H_2$ flow (100 sccm) and holding for 12 hours. A 500 mL syringe pump was used to introduce chemical grade n-heptane feed to the reactor. Gas chromatography analyses were performed to verify the feed composition before introduction to the catalyst bed. The feed was then pumped through the catalyst bed at a predetermined reaction temperature, a WHSV of 2 $hr^{-1}$, a hydrogen:hydrocarbon mole ratio of 2:1 and a pressure of 350 psig. The liquid products exiting the reactor flowed through heated lines. A gas chromatograph with FID detector was used for the analysis of product composition.

For all other reactions, the catalyst was activated in the reactor by heating to 300° C. at a ramp rate of 60° C./hr under $N_2$ flow (100 sccm), followed by a hold time of 1 hour. The temperature was then decreased to 220° C. at a 60° C./hr ramp rate. After reaching this temperature, the reactor was pressurized with $H_2$ at a back pressure of 350 psig and flow rate of 100 sccm for 3 hours. The temperature was then further decreased to 170° C. at a ramp rate of 60° C./hr. The $H_2$ flow rate was then set to 50.66 sccm at a back pressure of 180 psig, and these conditions were held for 1 hour.

For conducting isomerization reactions, hydrocarbon feed (s) were provided to the reactor using 500 mL ISCO syringe pumps. The hydrocarbon feeds were passed through a vaporizer and heated feed lines before entering the reactor. A Brooks mass flow controller was used to set the hydrogen flow rate, and a Grove back pressure controller was used to set the reactor pressure, typically at 350 psig. The hydrogen:hydrocarbon feed mole ratio was maintained at 2:1. Reaction temperatures and liquid hour space velocity (LHSV) values were regulated to attain a desired degree of conversion of the hydrocarbon feed. The product composition exiting the reactor was analyzed using an Agilent 7890 gas chromatograph.

Simultaneous screening of multiple samples was conducted using a multi-channel high throughput reactor. The reactor design facilitates equal flow of hydrogen and vaporized liquid hydrocarbons to each channel. The individual reactors defining each channel are held isothermally and isobarically. The products obtained from each channel were diluted with $N_2$ and analyzed by gas chromatography.

Isomerization Data of Normal Paraffin Feeds and Mixed Normal Paraffin Feeds

Example 1: Isomerization of n-Pentane. An n-pentane feed was isomerized at 190° C. and LHSV=2 $hr^{-1}$ under the general conditions specified above. Table 1 shows the product distribution obtained. The low cracking selectivity is expected for this feed.

TABLE 1

| Hydrocarbon Product | Weight Percent (%) |
| --- | --- |
| $CH_4 + C_2H_6$ | 0.02 |
| $C_3H_8$ | 0.28 |
| $i-C_4H_{10}$ | 1.13 |
| $n-C_4H_{10}$ | 0.28 |
| $i-C_5H_{12}$ | 70.7 |
| $n-C_5H_{12}$ | 25.8 |
| $C_6H_{14}$ | 1.72 |

TABLE 1-continued

| Hydrocarbon Product | Weight Percent (%) |
|---|---|
| i-$C_5$/Total $C_5$ (%) | 73.3 |
| Total Cracking Products $C_{4-}$ (%) | 1.71 |
| n-$C_5H_{12}$ conversion (%) | 74.2 |

Example 2: Isomerization of n-Hexane. An n-hexane feed was isomerized at 210° C. and LHSV=2 hr$^{-1}$ under the general conditions specified above. Table 2 shows the product distribution obtained. The low cracking selectivity is expected for this feed.

TABLE 2

| Hydrocarbon Product | Weight Percent (%) |
|---|---|
| $CH_4 + C_2H_6$ | 0.6 |
| $C_3H_8$ | 1.2 |
| i-$C_4H_{10}$ | 0.9 |
| n-$C_4H_{10}$ | 0.9 |
| i-$C_5H_{12}$ | 1.0 |
| n-$C_5H_{12}$ | 0.4 |
| 2,2-dimethylbutane | 24.4 |
| 2,3-dimethylbutane | 9.1 |
| 2-methylpentane | 29.6 |
| 3-methypentane | 18.2 |
| n-$C_6H_{14}$ | 13.4 |
| Total Cracking Products $C_{5-}$ (%) | 5.0 |
| n-$C_6H_{14}$ Conversion (%) | 86.6 |

Figure 2:
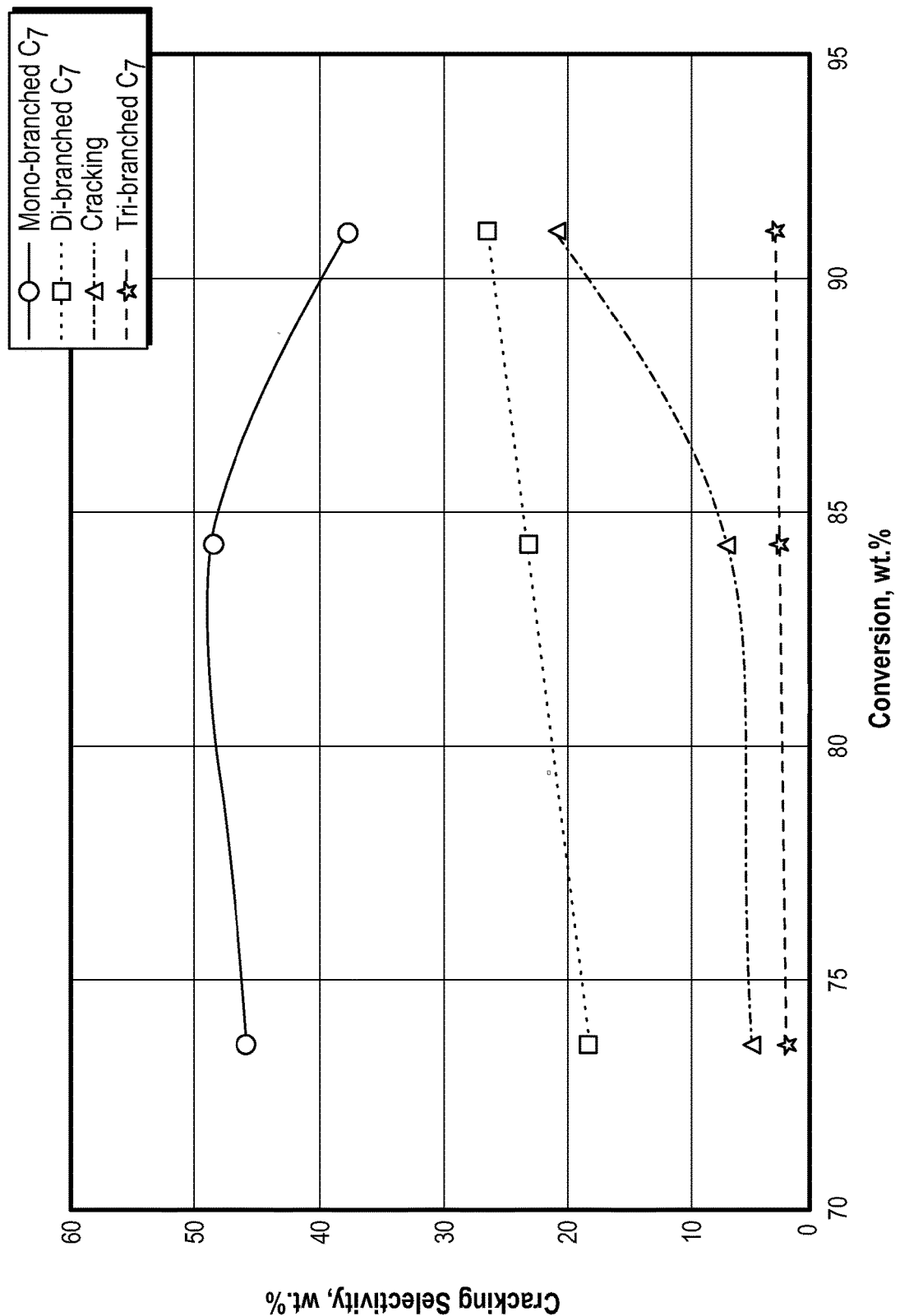
FIG. 2 is a plot of product distribution for an n-heptane feed at various conversion values under isomerization reaction conditions in the presence of a platinum-impregnated tungstated zirconium oxide catalyst.

Example 3: Isomerization of n-Heptane. An n-heptane feed was isomerized at 220° C. under the general conditions specified above at various LHSV values and corresponding conversion values. Table 3 shows the product distribution obtained in each case. As shown, the cracking selectivity decreased as the extent of conversion decreased. FIG. 2 is a plot of product distribution for an n-heptane feed at various conversion values under isomerization reaction conditions in the presence of a platinum-impregnated tungstated zirconium oxide catalyst.

TABLE 3

| | Weight Percent (%) | | |
|---|---|---|---|
| Hydrocarbon Product | LHSV = 1 hr$^{-1}$ | LHSV = 1.5 hr$^{-1}$ | LHSV = 2 hr$^{-1}$ |
| $CH_4$ | 0.05 | 0.02 | 0.01 |
| $C_2H_6$ | 0.11 | 0.05 | 0.04 |
| $C_3H_8$ | 8.78 | 2.92 | 2.09 |
| n-$C_4H_{10}$ | 0.62 | 0.28 | 0.19 |
| i-$C_4H_{10}$ | 10.76 | 3.72 | 2.67 |
| n-$C_5H_{12}$ | 0.11 | 0.07 | 0.05 |
| i-$C_5H_{12}$ | 0.20 | 0.08 | 0.06 |
| n-$C_6H_{14}$ | 0.05 | 0.00 | 0.00 |
| 2-methylpentane | 0.00 | 0.00 | 0.00 |
| 3-methylpentane | 0.05 | 0.01 | 0.00 |
| 2,2-dimethylbutane | 0.10 | 0.05 | 0.01 |
| n-$C_7H_{16}$ | 8.94 | 15.67 | 26.39 |
| 2-methylhexane | 19.13 | 24.47 | 23.08 |
| 3-methylhexane | 18.79 | 24.05 | 22.73 |
| 2,2-dimethylpentane | 8.12 | 4.69 | 2.70 |
| 2,3-dimethylpentane | 7.23 | 8.46 | 7.49 |
| 2,4-dimethylpentane | 6.50 | 7.85 | 6.84 |
| 3,3-dimethylpentane | 4.65 | 2.10 | 1.28 |
| 2,2,3-trimethylpentane | 1.88 | 1.04 | 0.72 |
| 1,3-dimethylcyclopentane | 1.29 | 1.66 | 1.63 |
| methylcyclohexane | 0.12 | 0.16 | 0.17 |
| Total cracking Products $C_{6-}$ (%) | 20.03 | 7.20 | 5.12 |
| n-$C_7H_{16}$ Conversion (%) | 91.06 | 84.33 | 73.61 |

Figure 3:
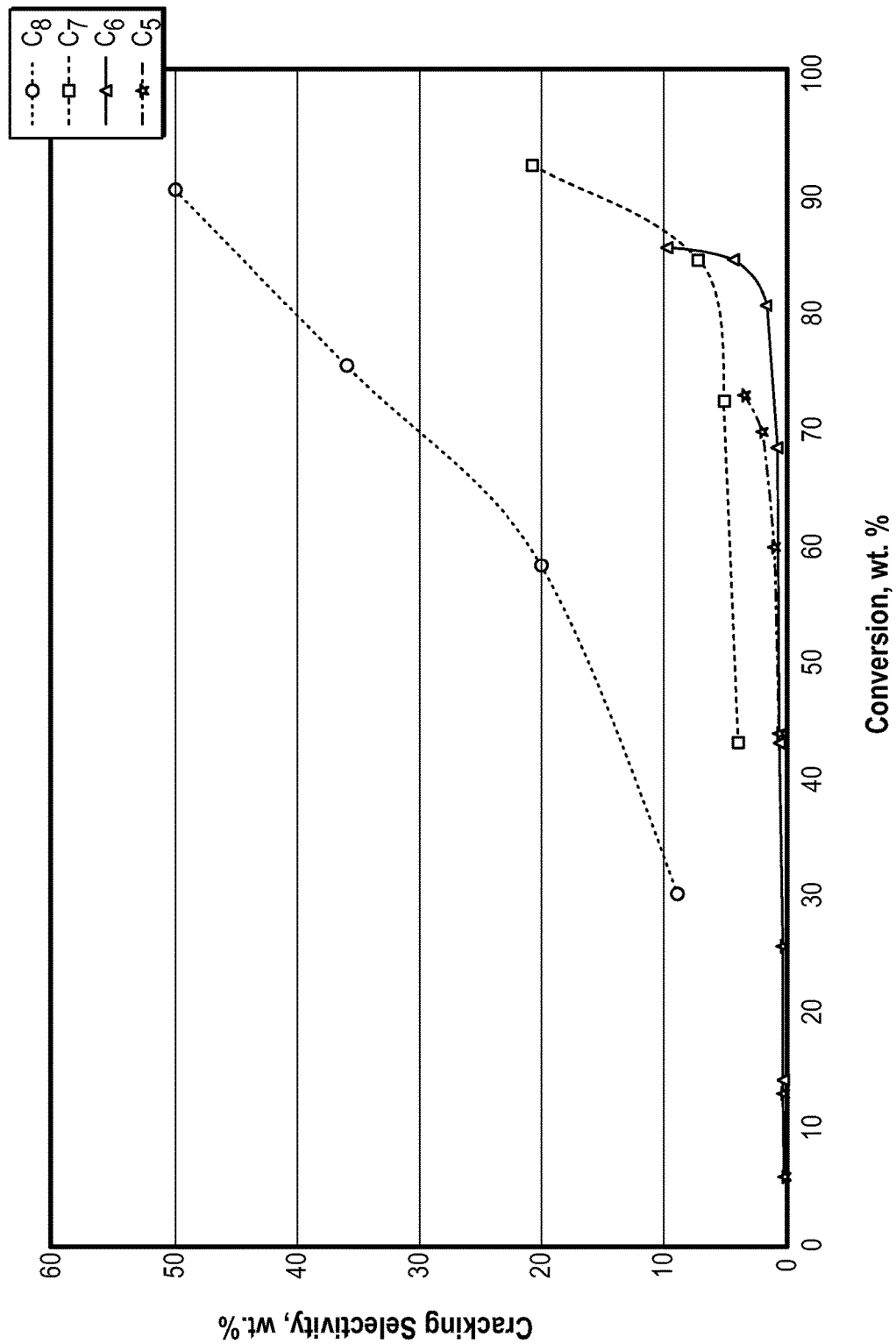
FIG. 3 is a plot of cracking selectivity for n-pentane, n-hexane, n-heptane and n-octane feeds obtained at various conversion values under isomerization reaction conditions in the presence of a platinum-impregnated tungstated zirconium oxide catalyst.

Example 4: Comparison of Cracking Selectivity for Various Normal Paraffins. n-Octane, n-heptane, n-hexane, and n-pentane were individually isomerized over a range of conversion values, and the cracking selectivity was determined at each conversion value. The cracking selectivity values represent the fraction of hydrocarbons in the product stream having a lower molecular weight than the parent hydrocarbon. FIG. 3 is a plot of cracking selectivity for n-pentane, n-hexane, n-heptane and n-octane feeds obtained at various conversion values under isomerization reaction conditions in the presence of a platinum-impregnated tungstated zirconium oxide catalyst. As shown, the cracking selectivity values for n-pentane and n-hexane were minimal at conversion values approaching 85%. n-Heptane displayed cracking selectivity at a higher baseline level (~5%) than did n-pentane or n-hexane, and the selectivity increased considerably above a conversion value of 85%. n-Octane displayed much higher cracking selectivity, even at low conversion values. For example, the lowest cracking selectivity measured for n-octane was slightly below 10% at 30% conversion, and the cracking selectivity increased progressively to about 50% at about 90% conversion. Thus, at the highest conversion values (~90-95%), n-octane displayed about 30% greater cracking selectivity than did n-heptane.

Figure 4:
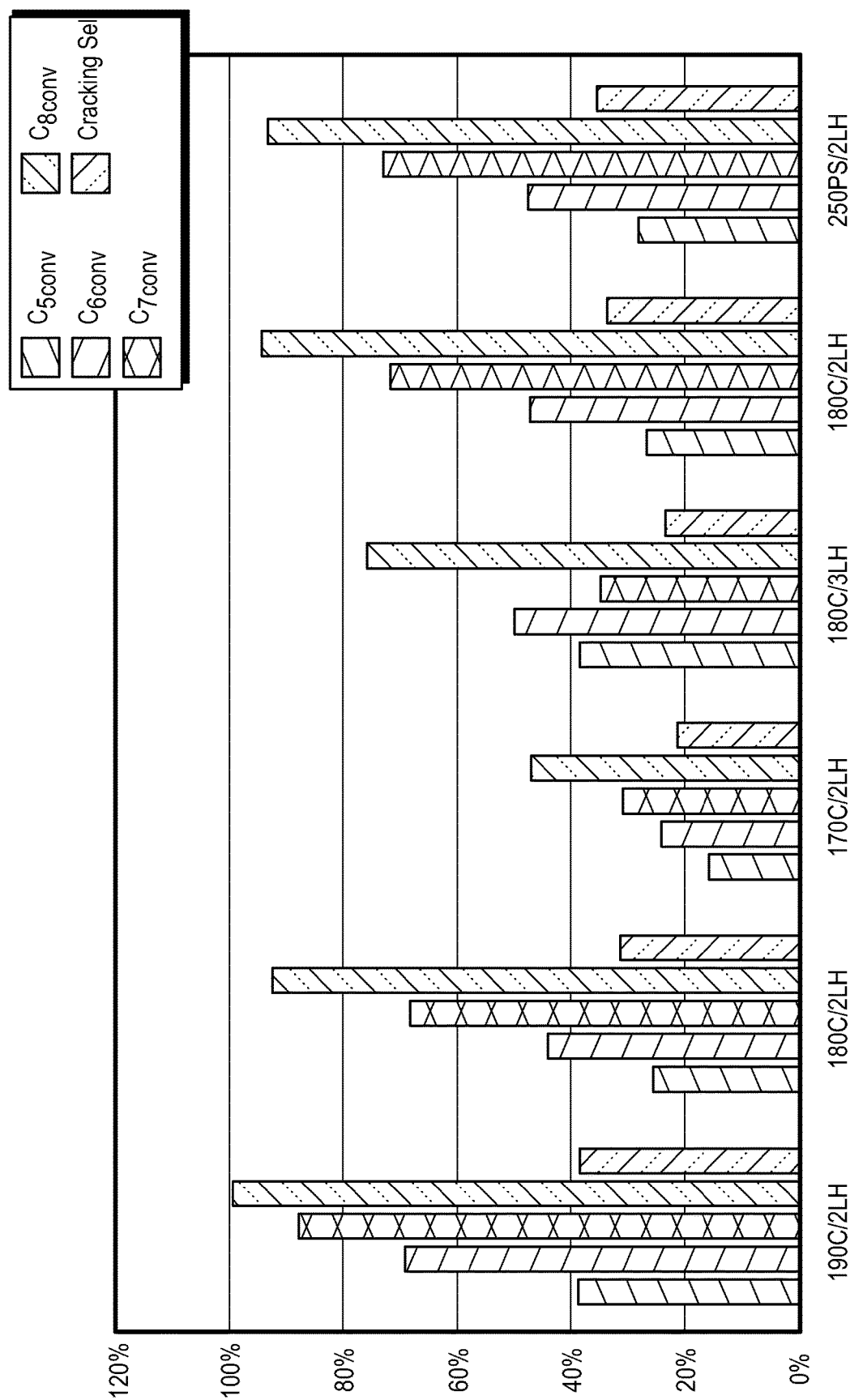
FIG. 4 is a bar graph of percent conversion for individual normal paraffins from a C5-C8 normal paraffin blend and the overall cracking selectivity obtained from the blend.

Example 5. Isomerization of a $C_5$-$C_8$ Normal Paraffin Blend. A 1:1:1:1 (wt. %) blend of n-pentane, n-hexane, n-heptane, and n-octane was isomerized at temperatures ranging from 170° C.-190° C., LHSV values of 1-3 hr$^{-1}$, and pressures ranging from 150-350 psig. FIG. 4 is a bar graph of percent conversion for individual normal paraffins from a $C_5$-$C_8$ normal paraffin blend and the overall cracking selectivity obtained from the blend. Of the normal paraffins, n-octane was the most extensively converted and n-pentane was the least extensively converted. In other words, n-octane reacted at the highest rate, and n-pentane reacted at the lowest rate. Surprisingly, the extent of cracking of the lighter normal paraffins did not increase appreciably at the higher temperatures used to crack the heavier normal paraffins n-heptane and n-octane. Even at the lowest percent conversion for n-octane, the cracking selectivity was still high (21% at 170° C. and 2 hr$^{-1}$ LHSV). Although the cracking selectivity was higher than desirable, the data does demonstrate that normal paraffin blends may undergo isomerization.

Figure 5:
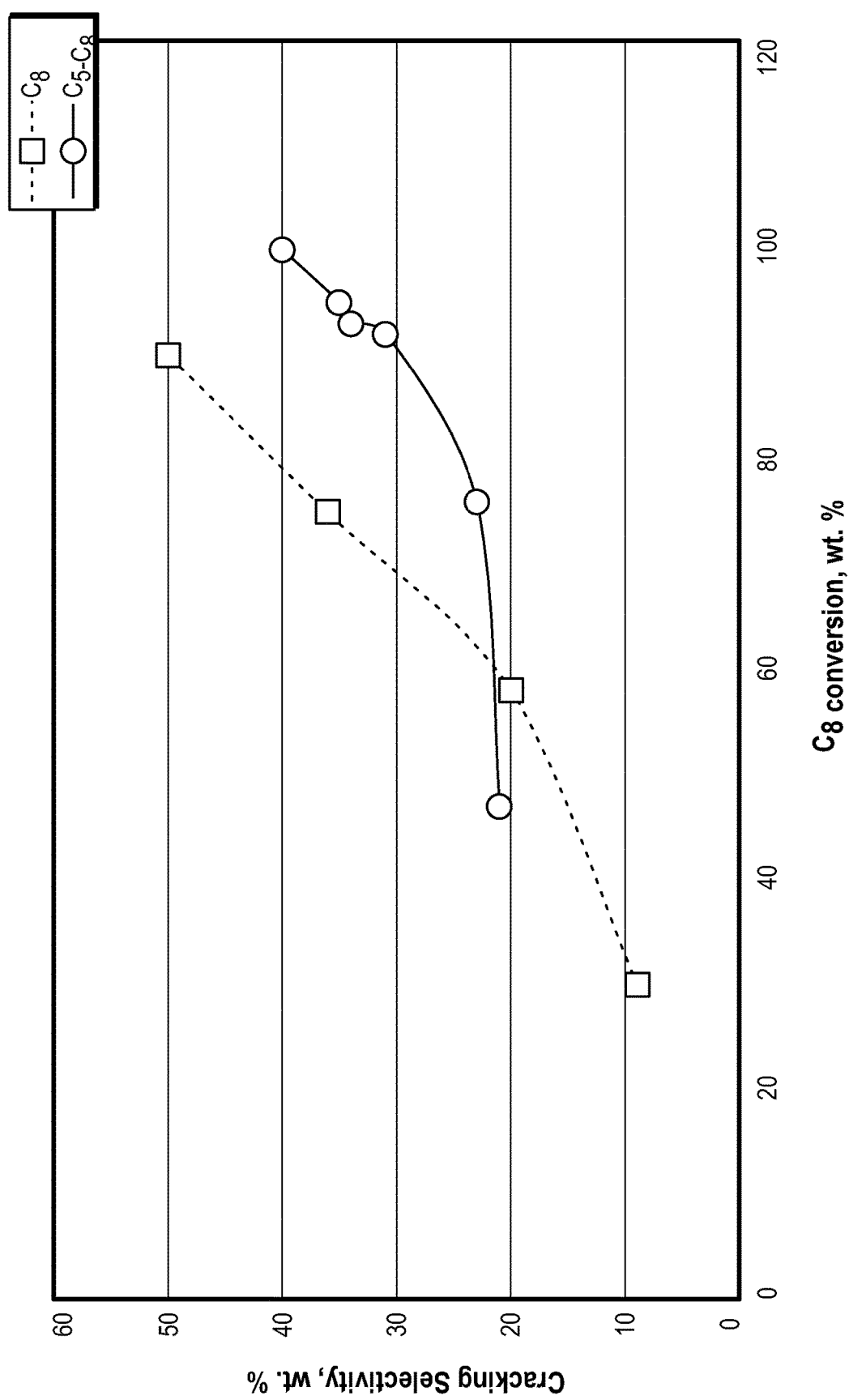
FIG. 5 is a plot of cracking selectivity as a function of C8 normal paraffin conversion for a C5-C8 normal paraffin blend and C8 normal paraffin alone.

FIG. 5 is a plot of cracking selectivity as a function of $C_8$ normal paraffin conversion for a $C_5$-$C_8$ normal paraffin blend and $C_8$ normal paraffin alone. As shown, the cracking selectivity was lower in the $C_5$-$C_8$ normal paraffin blend than when the $C_8$ normal paraffin alone was isomerized. This trend continues in normal paraffin blends lacking $C_8$ normal paraffins, as shown in the next example.

Figure 6:
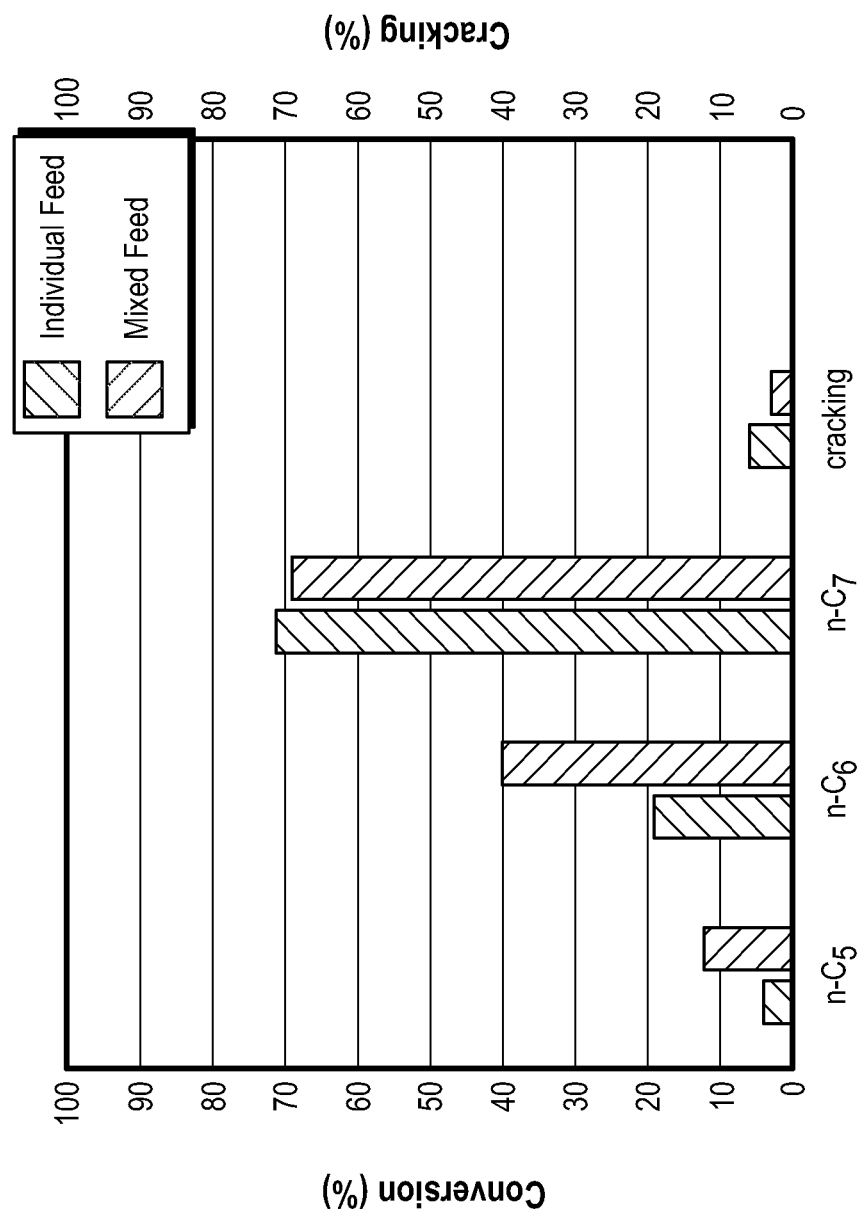
FIG. 6 is a bar graph of percent conversion and cracking selectivity for individual C5-C7 normal paraffins and for a C5-C7 normal paraffin blend.

Example 6. Isomerization of a $C_5$-$C_7$ Normal Paraffin Blend. A 1:1:1 (wt. %) blend of n-pentane, n-hexane, and n-heptane was isomerized at a temperature of 170° C., a pressure of 200 psig, and a LHSV value of 2 hr$^{-1}$. Individual feeds of n-pentane, n-hexane and n-heptane were also isomerized under identical conditions for comparison. Conversion percentages and cracking selectivity values are shown in Table 4, and the data is also plotted in FIG. 6.

TABLE 4

| | Product | | | Cracking Selectivity |
|---|---|---|---|---|
| Feed | i-$C_5H_{12}$ | i-$C_6H_{14}$ | i-$C_7H_{16}$ | (%) |
| n-$C_5H_{12}$ | 4 | | | |
| n-$C_6H_{14}$ | | 19 | | |
| n-$C_7H_{16}$ | | | 71 | 6 |

TABLE 4-continued

| Feed | Product | | | Cracking Selectivity (%) |
|---|---|---|---|---|
| | i-$C_5H_{12}$ | i-$C_6H_{14}$ | i-$C_7H_{16}$ | |
| n-$C_5H_{12}$/ n-$C_6H_{14}$/n-$C_7H_{16}$ (1:1:1) | 12 | 40 | 69 | 3 |

As shown, the conversion percentage for n-pentane and n-hexane surprisingly increased 2- to 3-fold in the $C_5$-$C_7$ normal paraffin blend, while the conversion percentage for n-heptane remained about the same. Moreover, the overall extent of cracking in the $C_5$-$C_7$ normal paraffin blend decreased by about half. Unlike the $C_5$-$C_8$ normal paraffin blend (Example 5), the extent of cracking is much more manageable when processing a $C_5$-$C_7$ normal paraffin blend.

Figure 7:
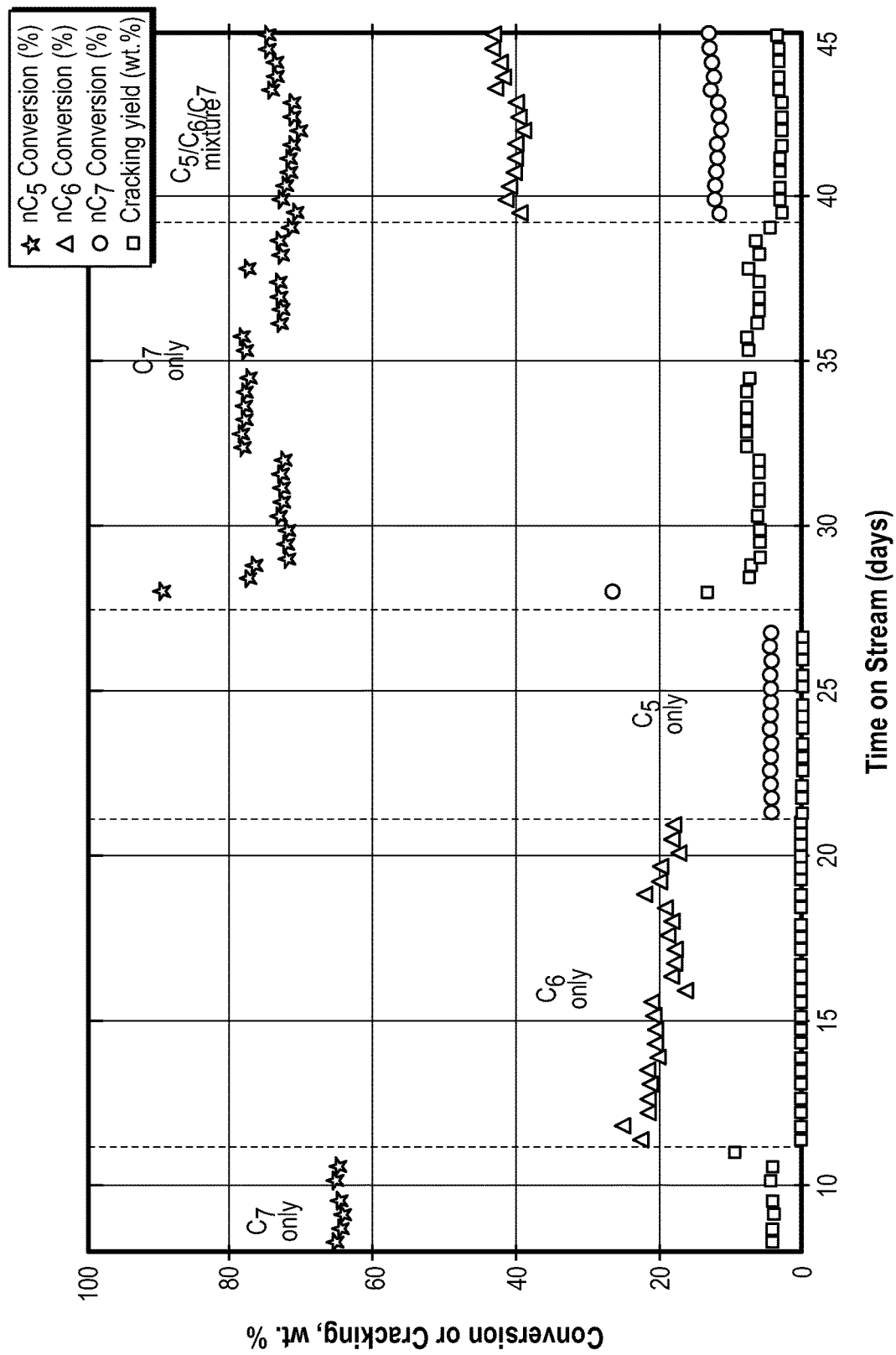
FIG. 7 is a plot of conversion and cracking selectivity for a C5-C7 normal paraffin blend and individual normal paraffin feeds at various time on stream values.

Individual feeds of n-heptane, n-hexane, h-pentane, n-heptane, and a $C_5$-$C_7$ normal paraffin blend were sequentially exposed to the isomerization reaction conditions, and the conversion and cracking selectivity were plotted as a function of time on stream (FIG. 7). As shown, n-pentane and n-hexane conversion were again higher when the $C_5$-$C_7$ normal paraffin blend was isomerized, and the cracking selectivity was lower.

Figure 8:
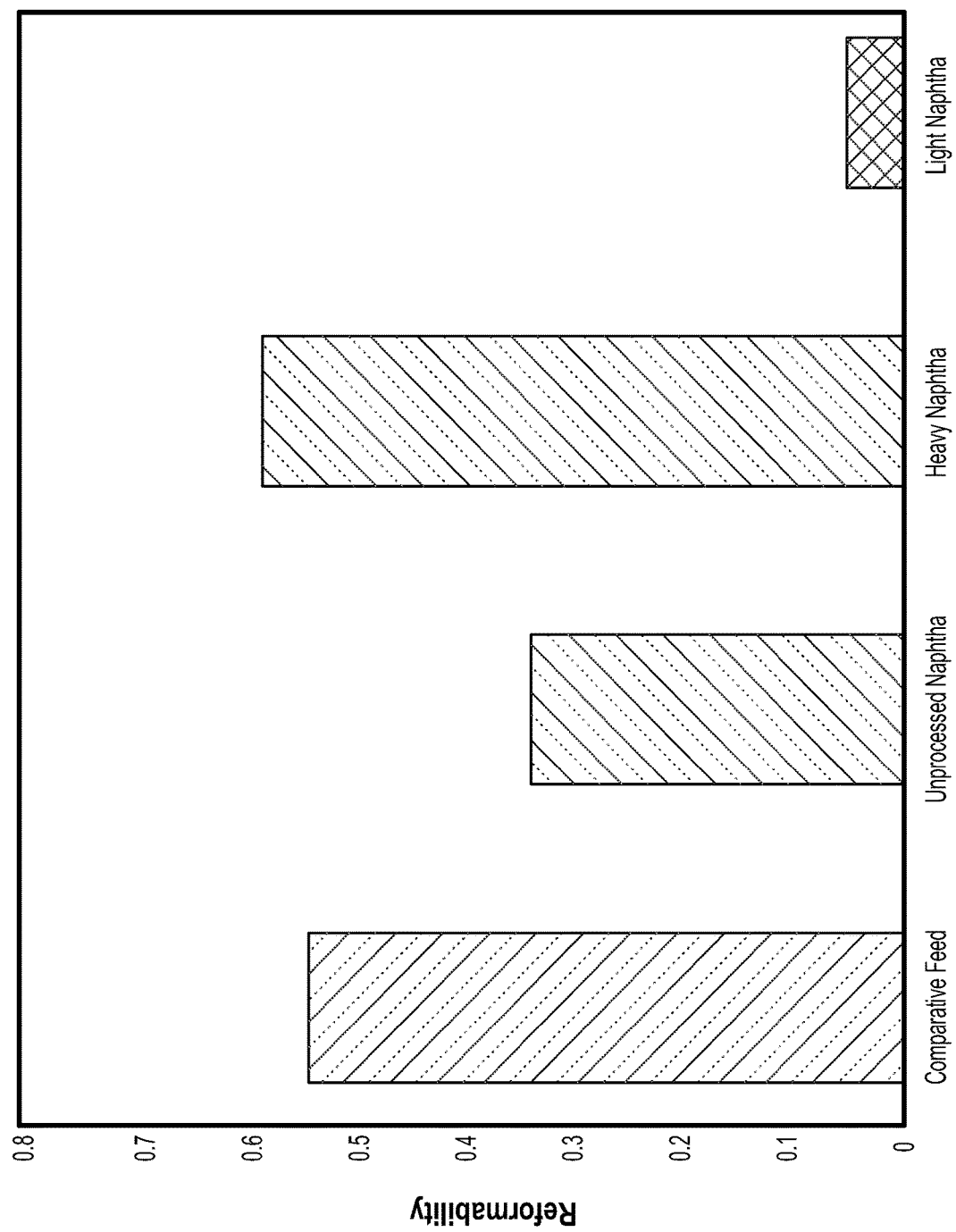
FIG. 8 is a plot reformability factor for an unprocessed naphtha, distilled heavy naphtha, and distilled light naphtha in comparison to a feed typically used in continuous catalytic reforming processes.

Example 7. Naphtha Separation into Light Naphtha and Heavy Naphtha, Followed by Isomerization and Reforming. A naphtha stream having a boiling point range of 96-370° F. (35-188° C.) was fractionated at a cut point of 210° F. (99° C.) into a light naphtha fraction having a boiling point range of 96-210° F. (35-99° C.) and a heavy naphtha fraction having a boiling point range of 210-370° F. (99-188° C.). At this cut point, a majority of the n-heptane was fractionated into the light naphtha fraction. A minority component of the n-heptane may reside in the heavy naphtha fraction. The decreased n-heptane content of the heavy naphtha feed resulted in a higher reformability factor as a consequence of a higher weight percentage of naphthenic compounds in the heavy naphtha fraction. The higher reformability factor is characteristic of easier catalytic reforming. FIG. 8 is a plot reformability factor for an unprocessed naphtha, distilled heavy naphtha, and distilled light naphtha in comparison to a feed typically used in continuous catalytic reforming processes. As shown, the unprocessed naphtha had a poorer formability factor than did the comparative feed. In contrast, the heavy naphtha had a significantly improved reformability factor, even greater than that of the comparative feed. By excluding a majority of the $C_7$ hydrocarbons from the heavy naphtha, the feed becomes much easier to reform to produce aromatic compounds. Although the reformability factor of the light naphtha is low, this feed may be processed through isomerization, as discussed above.

Table 5 shows simulated reforming data for the comparative reforming feed, simulated reforming data for the heavy naphtha feed, and simulated isomerization data for the light naphtha feed. Internal process models were used for modeling both the reforming and isomerization processes. The two process models were tuned using commercial reforming unit and pilot plant isomerization process. Research Octane Number (RON) and Motor Octane Number (MON) values were determined according to Ghosh, P., et al., *Ind. Eng. Chem. Res.*, 2006, pp. 337-345, 45.

TABLE 5

| | Comparative Feed Reforming | Heavy Naphtha Reforming | Light Naphtha Isomerization |
|---|---|---|---|
| Rate (MBPD) | 65 | 63.8 | 35.8 |
| Furnace Duty (MMBTU/hr) | 324 | 324 | — |
| Initial RON/MON | 61/61 | 56/56 | 64/64 |
| Final RON/MON | 100/90 | 100/89 | 81/77 |
| Blended liquid RON/MON | — | 93/85 | |
| Liquid Yield (wt. %) | 86.8 | 86.5 | 95 |
| Overall Liquid Yield (wt. %) | 86.8 | 89.4 | |
| Total Throughput (MBPD) | 65 | 96 | |
| Benzene (wt. %) | 2.3 | 2.0 | 0 |
| Toluene (wt. %) | 10.0 | 11.9 | 0 |
| Xylene (wt. %) | 19.3 | 18.7 | 0 |
| Ethylbenzene (wt. %) | 4.7 | 4.9 | 0 |

Thus, by separating a naphtha stream into light naphtha comprising predominantly $C_{7-}$ hydrocarbons and heavy naphtha comprising predominantly $C_{8+}$ hydrocarbons, a combined reformed/isomerized product having similar characteristics to a conventional catalytic reforming process may be obtained.

Isomerization in the Presence of Naphthenic Compounds

Figure 9:
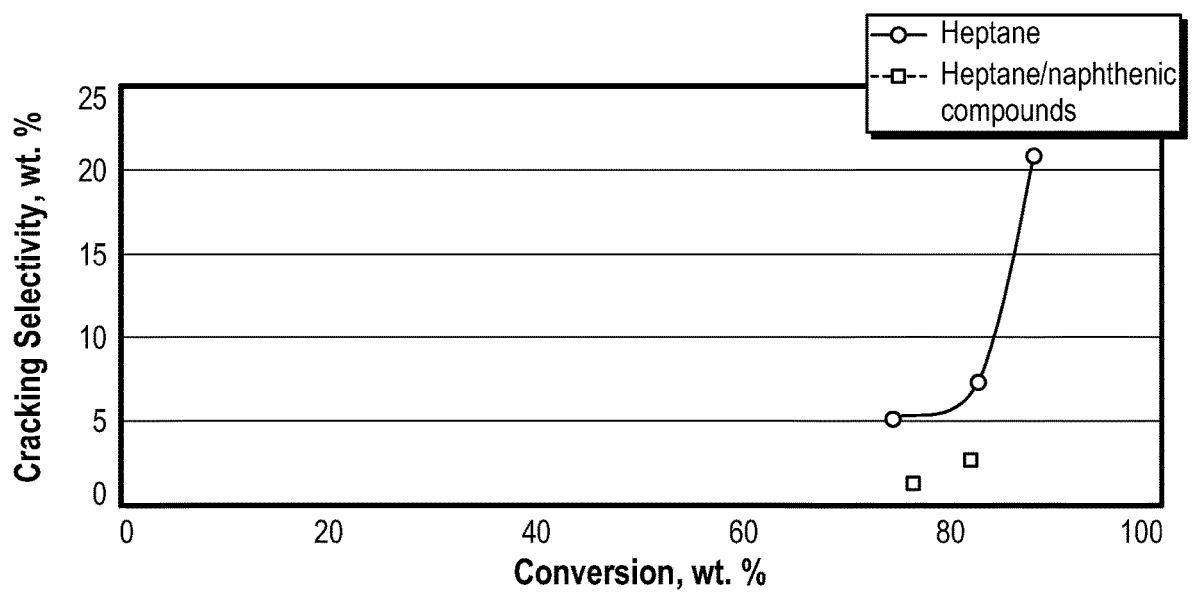
FIG. 9 is a plot of cracking selectivity for a 1:1 (w/w) feed of n-heptane:naphthenic compounds obtained under isomerization reaction conditions in the presence of a platinum-impregnated tungstated zirconium oxide catalyst.
Figure 10:
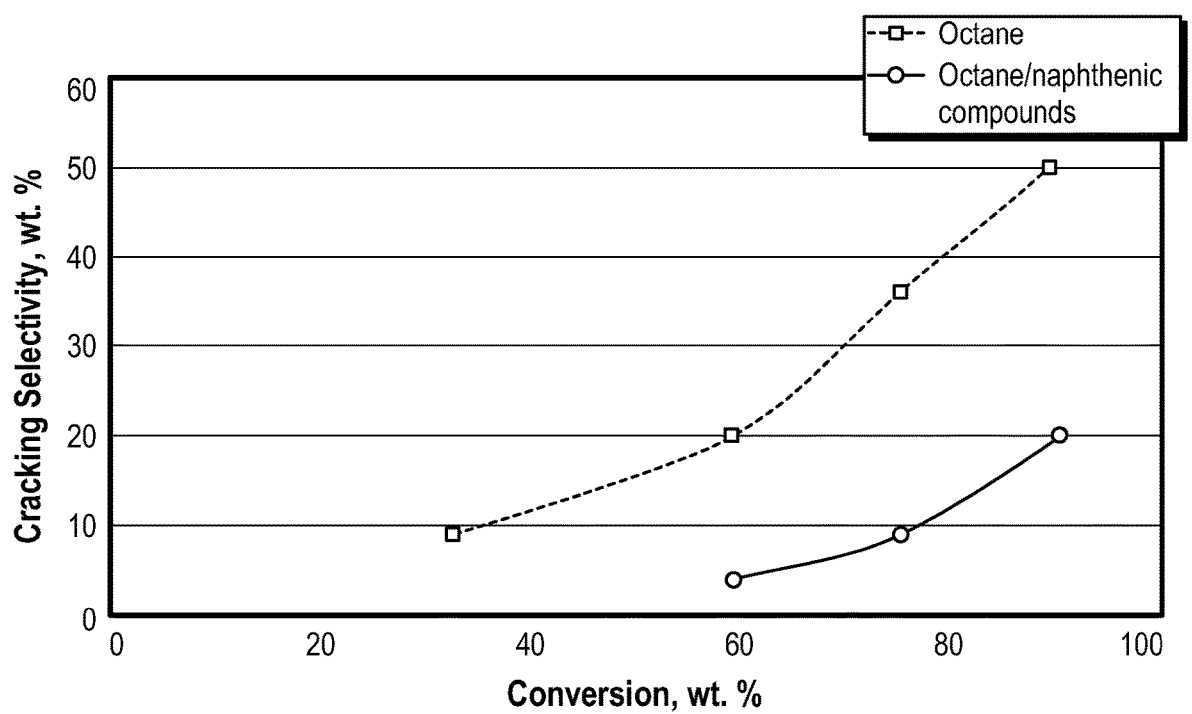
FIG. 10 is a plot of cracking selectivity for a 1:1 (w/w) feed of n-octane:naphthenic compounds obtained under isomerization reaction conditions in the presence of a platinum-impregnated tungstated zirconium oxide catalyst.

Example 8: Isomerization of n-Heptane and n-Octane in the Presence of Naphthenic Compounds. Example 4 was repeated over a range of conversion values, except a 1:1 blend of n-heptane or n-octane and naphthenic compounds (1:1 mixture of methylcyclopentane and methylcyclohexane; 2:1:1 blend of normal paraffin:methylcyclopentane:methylcyclohexane, all on a weight basis) was utilized as the feed. FIG. 9 is a plot of cracking selectivity for a 1:1 (w/w) feed of n-heptane:naphthenic compounds obtained under isomerization reaction conditions in the presence of a platinum-impregnated tungstated zirconium oxide catalyst. Similarly, FIG. 10 is a plot of cracking selectivity for a 1:1 (w/w) feed of n-octane:naphthenic compounds obtained under isomerization reaction conditions in the presence of a platinum-impregnated tungstated zirconium oxide catalyst. In both plots, the corresponding cracking selectivity data for each normal paraffin feed alone is presented for comparison (see FIG. 3). Like the normal paraffins alone, cracking selectivity (increased extent of cracking) was greater at higher conversion values for both n-heptane and n-octane in the presence of naphthenic compounds, but the cracking selectivity was considerably decreased compared to that occurring when the naphthenic compounds were omitted. Conversion values represent the fraction of n-heptane or n-octane converted to products or cracked.

Tables 6 and 7 below show the percentage conversion for each component in the 1:1 blends of normal paraffins and naphthenic compounds that were isomerized according to this example. The data in Table 6 was obtained at 2.75 wt. % cracking selectivity for n-heptane, and the data in Table 7 was obtained at 7 wt. % cracking selectivity for n-octane. Conversion values are based upon the amount of recovered feed mixture component divided by the amount of feed mixture component input to the reactor. As shown, the normal paraffins were isomerized to a much greater extent than were the naphthenic compounds co-fed therewith.

TABLE 6

| Feed Component | % Conversion (at 2.75 wt. % cracking selectivity) |
|---|---|
| n-heptane (50 wt. % of feed) | 83 |
| methylcyclopentane (25 wt. % of feed) | 31 |
| methylcyclohexane (25 wt. % of feed) | 38.5 |

TABLE 7

| Feed Component | % Conversion (at 9 wt. % cracking selectivity) |
|---|---|
| n-octane (50 wt. % of feed) | 75 |
| methylcyclopentane (25 wt. % of feed) | 41 |
| methylcyclohexane (25 wt. % of feed) | 30 |

Figure 11:
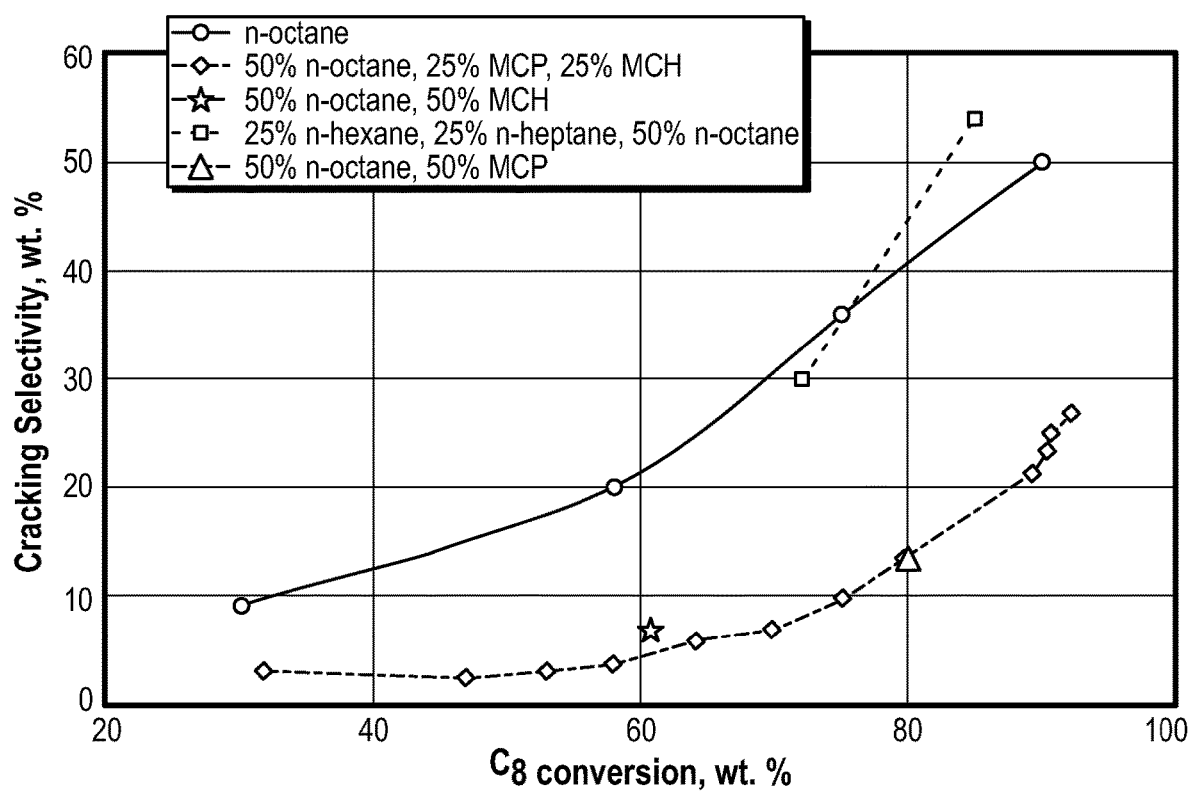
FIG. 11 is a plot of cracking selectivity for various n-octane feeds containing or lacking naphthenic compounds obtained under isomerization reaction conditions in the presence of a platinum-impregnated tungstated zirconium oxide catalyst.
Figure 12:
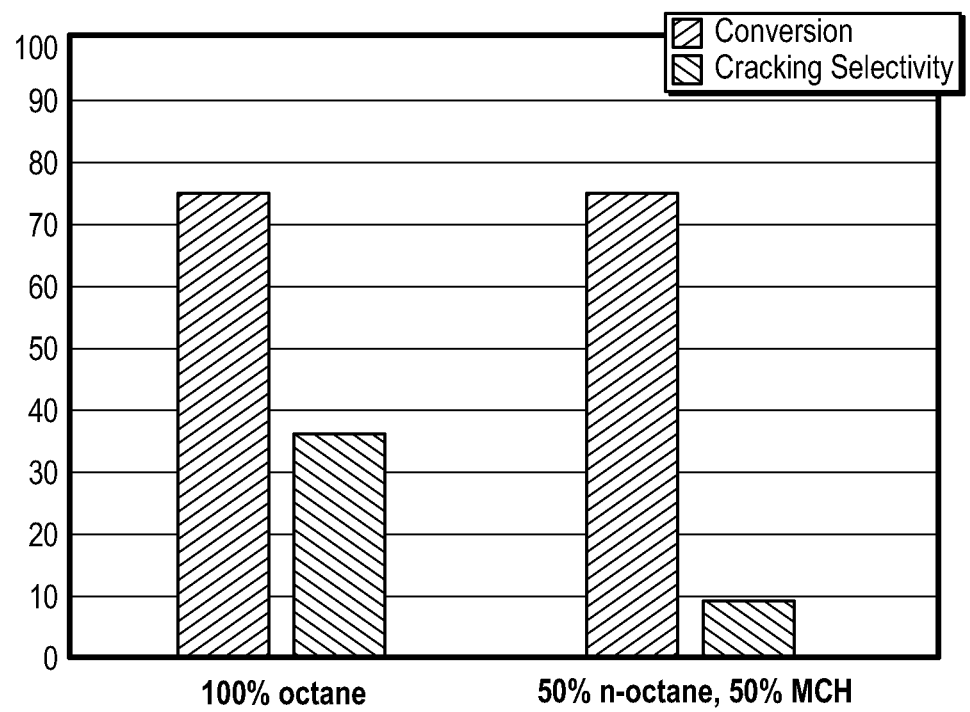
FIG. 12 is a bar graph showing the variance of cracking selectivity and percent conversion under isomerization reaction conditions in the presence of a platinum-impregnated tungstated zirconium oxide catalyst for n-octane alone and a 1:1 blend of n-octane and methylcyclohexane.

Example 9: Isomerization of n-Octane in the Presence of Varying Ratios of Naphthenic Compounds. Example 8 was repeated, except the composition of naphthenic compounds blended with the normal paraffin was varied. Only n-octane or n-octane blends were tested in this example, and the ratio of n-octane to naphthenic compounds was maintained at 1:1 in all cases, except for samples purposefully omitting the naphthenic compounds. The following feeds or feed mixtures were tested in this example: n-octane (no naphthenic compound co-feed); 50% n-octane, 25% n-hexane, and 25% n-heptane (no naphthenic compound co-feed); 50% n-octane, 25% methylcyclopentane, and 25% methylcyclohexane; 50% n-octane and 50% methylcyclohexane; and 50% n-octane and 50% methylcyclopentane. FIG. 11 is a plot of cracking selectivity for various n-octane feeds containing or lacking naphthenic compounds obtained under isomerization reaction conditions in the presence of a platinum-impregnated tungstated zirconium oxide catalyst. As shown, both n-octane alone and a blend of $C_6$-$C_8$ normal paraffins lacking naphthenic compounds experienced significant cracking under the isomerization reaction conditions, much more so than did any of the n-octane blends containing various naphthenic compounds. Methylcyclopentane or methylcyclohexane alone afforded a degree of cracking selectivity comparable to that of a 1:1 blend of the two naphthenic compounds. FIG. 12 is a bar graph showing the variance of cracking selectivity and percent conversion under isomerization reaction conditions in the presence of a platinum-impregnated tungstated zirconium oxide catalyst for n-octane alone and a 1:1 blend of n-octane and methylcyclohexane. As shown, the cracking selectivity was nearly four-fold lower in the presence of methycyclohexane at a comparable conversion percentage.

Figure 13A:
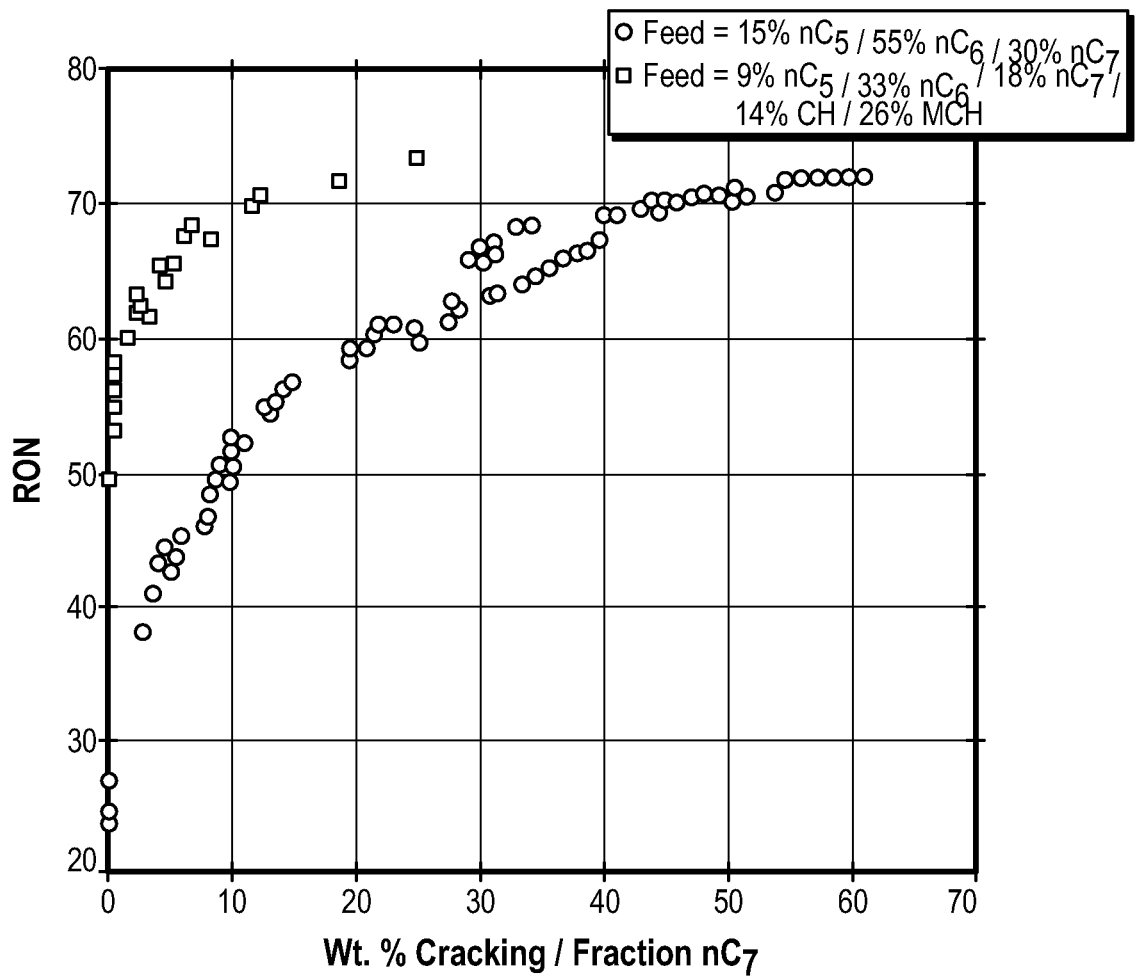
FIGS. 13A, 13B and 13C are graphs showing, respectively, calculated research octane number (RON), n-heptane conversion and relative n-heptane conversion obtained under isomerization reaction conditions in the presence of a platinum-impregnated tungstated zirconium oxide catalyst for n-heptane feed mixtures lacking or containing naphthenic compounds.
Figure 13B:
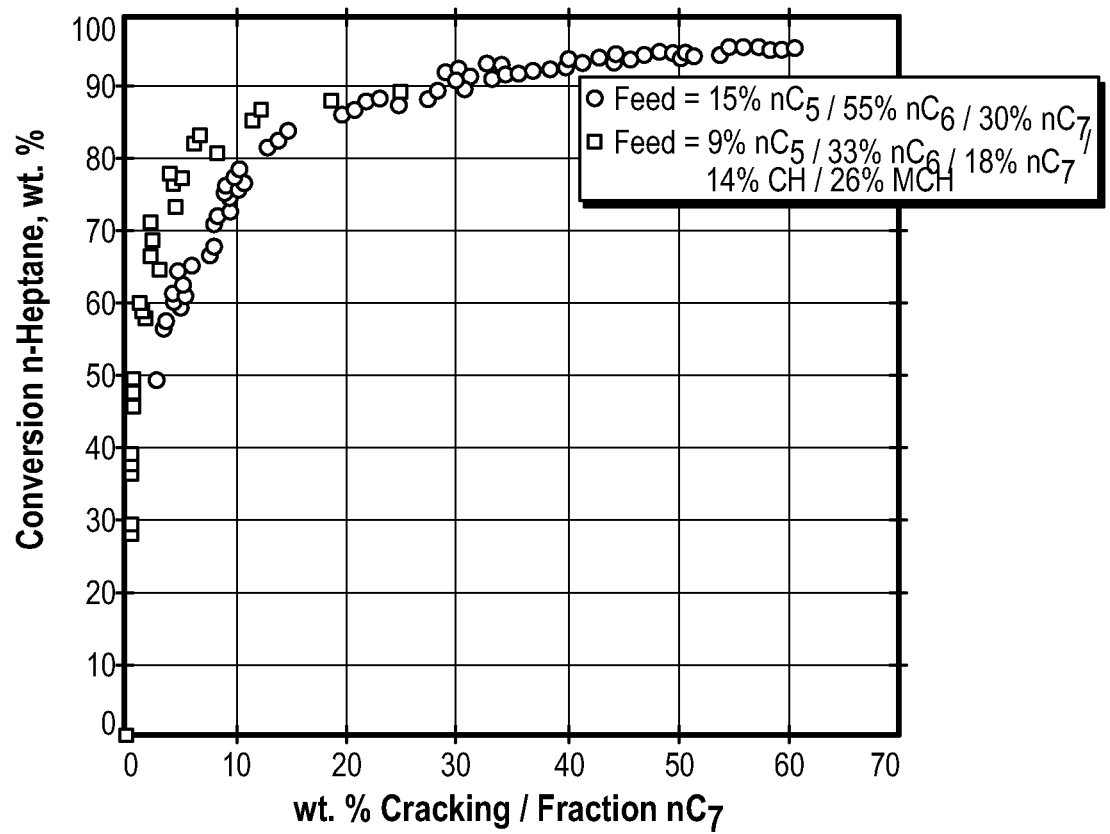
Figure 13C:
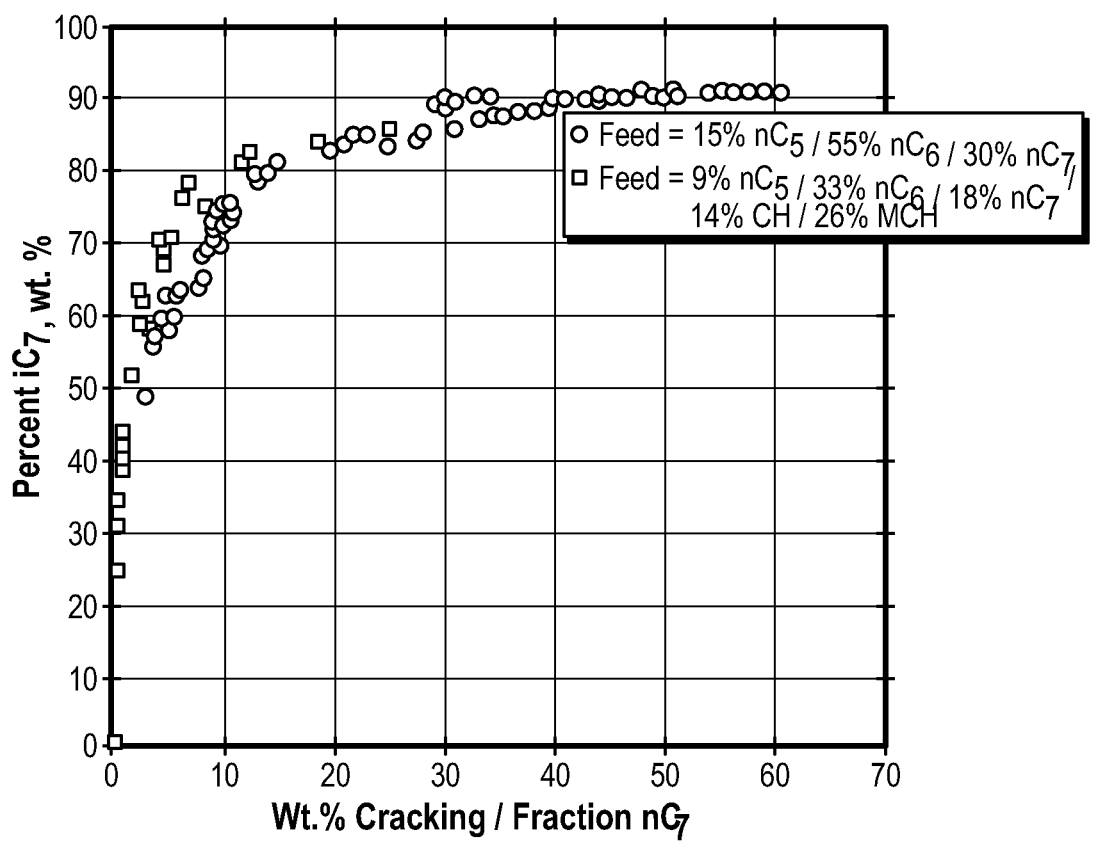

Example 10: Isomerization of n-Heptane Feeds in the Presence of Naphthenic Compounds. Example 8 was repeated under isomerization reaction conditions in a high-throughput reactor and with several alternative preparations of the above-referenced bifunctional mixed metal oxide catalyst (catalyst preparations not shown). The following feed mixtures were tested in this example: 15% n-pentane, 55% n-hexane, and 30% n-heptane; and 9% n-pentane, 33% n-hexane, 18% n-heptane, 14% cyclohexane, and 26% methylcyclohexane. FIGS. 13A, 13B and 13C are plots showing, respectively, calculated research octane number (RON), n-heptane conversion and relative n-heptane conversion obtained under isomerization reaction conditions in the presence of a platinum-impregnated tungstated zirconium oxide catalyst for n-heptane feed mixtures lacking or containing naphthenic compounds. The data is aggregated for all tested alternative catalyst preparations. As shown, the n-heptane feed mixture containing naphthenic compounds afforded superior properties compared to the n-heptane feed mixture lacking the naphthenic compounds.

Figure 14:
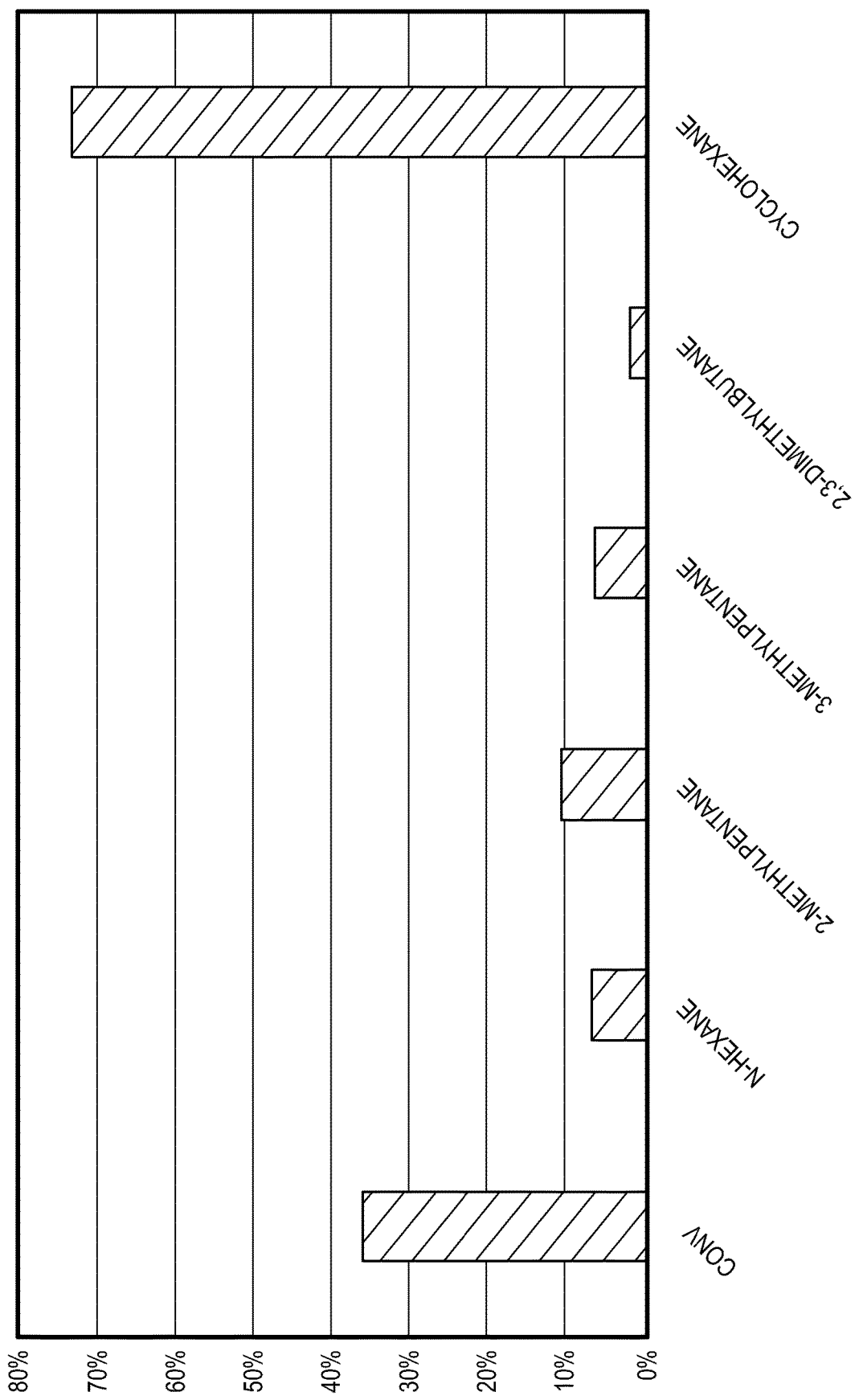
FIG. 14 is a bar graph of the product distribution obtained from a 1:1 blend of n-heptane/methylcyclopentane under isomerization reaction conditions in the presence of a platinum-impregnated tungstated zirconium oxide catalyst.
Figure 15:
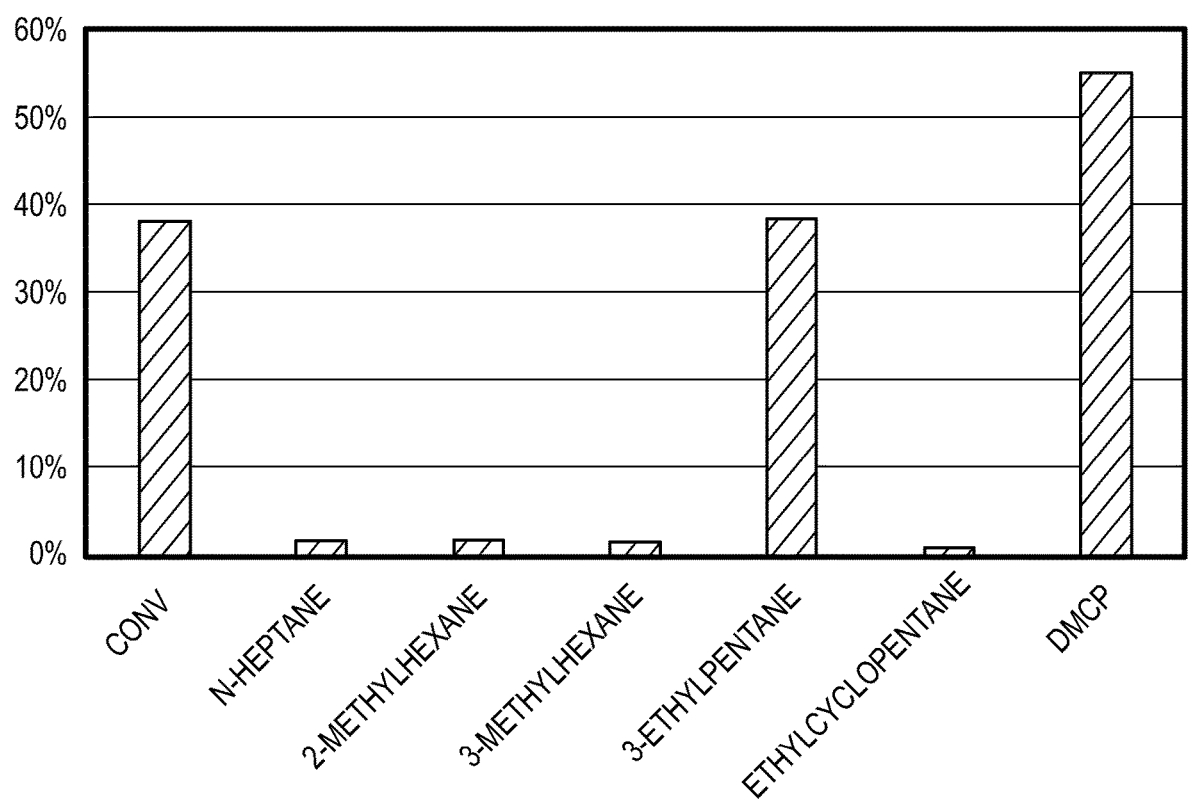
FIG. 15 is a bar graph of the product distribution obtained from a 1:1 blend of n-octane/methylcyclohexane under isomerization reaction conditions in the presence of a platinum-impregnated tungstated zirconium oxide catalyst.
Figure 16:
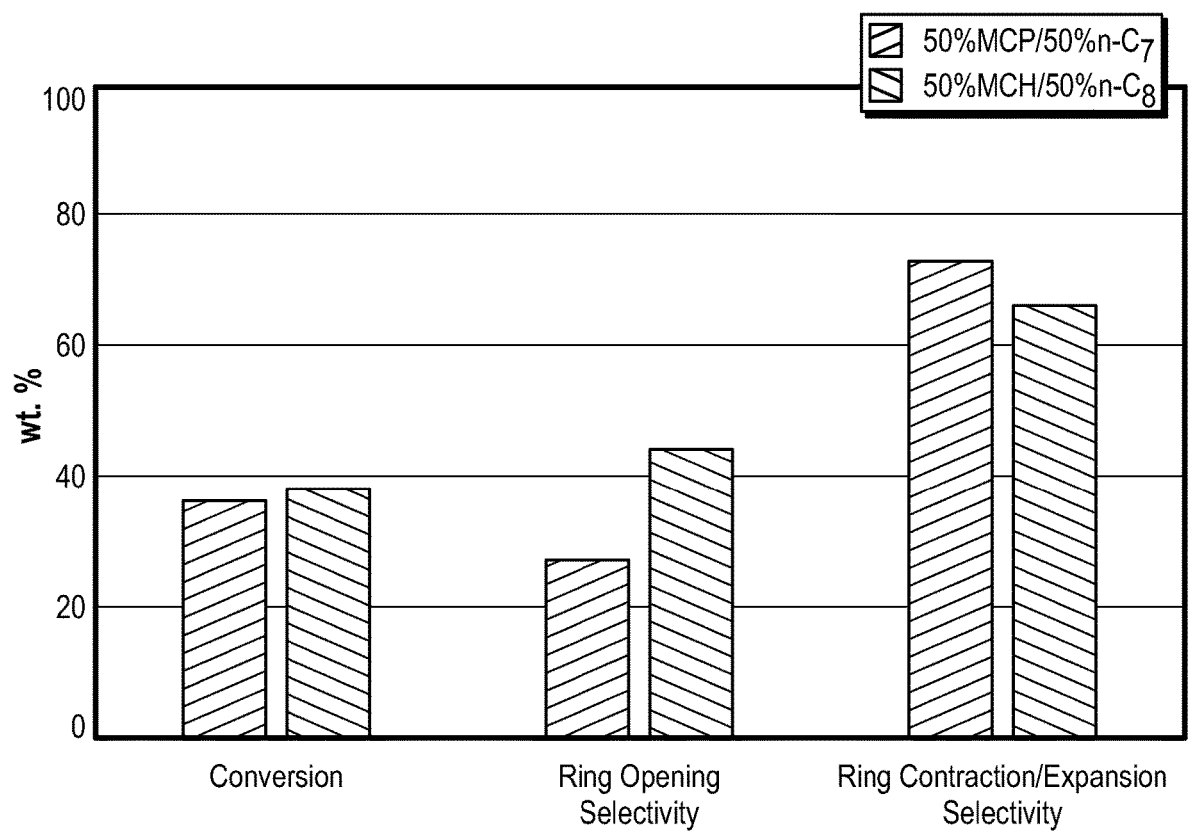
FIG. 16 is a bar graph showing the breakdown between ring opening and ring expansion or contraction for methylcyclopentane and methylcyclohexane under isomerization reaction conditions in the presence of a platinum-impregnated tungstated zirconium oxide catalyst.

Example 11: Product Distribution of n-Heptane and n-Octane Feed Mixtures Containing Naphthenic Compounds. 1:1 blends of n-heptane/methylcyclopentane and n-octane/methylcyclohexane were isomerized under the conditions specified above. The product distribution in each case was determined. FIG. 14 is a bar graph of the product distribution obtained from a 1:1 blend of n-heptane/methylcyclopentane under isomerization reaction conditions in the presence of a platinum-impregnated tungstated zirconium oxide catalyst, and FIG. 15 is a bar graph of the product distribution obtained from a 1:1 blend of n-octane/methylcyclohexane under isomerization reaction conditions in the presence of a platinum-impregnated tungstated zirconium oxide catalyst. As shown, cyclohexane was the predominant product obtained when isomerizing n-heptane/methylcyclopentane, and when isomerizing n-octane/methylcyclohexane, 3-ethylpentane and dimethylcyclopentane were both obtained in significant quantities. Thus, depending on the naphthenic compound employed, ring expansion and/or contraction/isomerization of the naphthenic compounds may occur under the isomerization reaction conditions. Ring opening may occur to a lesser degree. FIG. 16 is a bar graph showing the breakdown between ring opening and ring expansion or contraction for methylcyclopentane and methylcyclohexane under isomerization reaction conditions in the presence of a platinum-impregnated tungstated zirconium oxide catalyst. As shown, methylcyclopentane and methylcyclohexane both primarily underwent ring expansion or contraction/isomerization in preference to ring opening. Methylcyclopentane primarily underwent ring expansion, whereas methylcyclohexane primarily underwent ring contraction and subsequent isomerization.

Isomerization in the Presence of a Bifunctional Mixed Metal Oxide Catalyst Promoting Decreased Cracking In this set of experiments, the performance of the catalyst described above was compared to that of a catalyst promoting a decreased extent of cracking. The previously described catalyst nominally contains 16 wt. % W, whereas the alternative catalyst preparation nominally contains 13 wt. % W, and other parameters are substantially the same. The catalyst containing 13 wt. % W was synthesized in the following manner.

13 wt. % W Mixed Metal Oxide Preparation. Preparation of solution A: In a beaker, 181.8 grams of concentrated $NH_4OH$ and 28.0 grams of $(NH_4)_6H_2W_{12}O_{40} \cdot xH_2O$ (66.9% W) (ammonium metatungstate, AMT) were combined with stirring in 248 ml of $H_2O$, and heated to 60° C. Preparation of solution B: 345 grams of $ZrOCl_2 \cdot xH_2O$ and 5.3 grams of $FeSO_4$ were dissolved in 284 ml of $H_2O$ and heated at 60° C. In a separate vessel, 525 grams of de-ionized water was adjusted to a pH of 9-10 with $NH_4OH$. The alkaline solution was stirred at 40° C. While stirring, solutions A and B were added to the alkaline solution at 10 ml/minute. After the complete addition of solutions A and B, the slurry was stirred for an hour at 40° C. At the completion of the co-precipitation, the slurry was transferred to a polypropylene bottle or Teflon bottle, and digested for 72 hours at 23°

C.-25° C. After digestion, the resulting powder was filtered and washed with water. The powder at this point may or may not be washed with NH$_4$NO$_3$. The powder was washed with additional water, and dried at 120° C. The powder was then calcined in air in a temperature range from 700° C.-850° C. to prepare the active oxide form of the powder, which was composed of 0.7 wt. % Fe, 13 wt. % W, and 56 wt. % Zr. The peak height ratio from powder x-ray diffraction of monoclinic tungsten oxide:monoclinic zirconium oxide was 0.31 after calcination at 750° C.

Extrusion conditions. Extrusion was conducted in a similar manner for the 13 wt. % W and 16 wt. % W catalyst samples. Self-bound extrusion of powder samples was carried out on a 1" Diamond America extruder using 100 g of powder mulled for 5 minutes in a Lancaster muller. Following an initial mulling period, 10 g of ABITEC CAPLUBE® ethoxylated castor oil, was added to the mulled powder, and mulling was conducted for an additional 5 minutes. A sufficient amount of water was then added to form a paste for extrusion of 1/16" quadrulobes. After extrusion, the extrudates were dried at 120° C. for several hours. The extrudates may or may not be washed with NH$_4$NO$_3$. After drying, the extrudates were calcined at 1000° F. (537.7° C.) for 4 hours to prepare the final extrudates. Typical crush strengths for this type of extrudate ranged from 50 lbs/in to 60 lbs/in.

Pt Impregnation. Pt impregnation was conducted in a similar manner for both samples prior to conducting isomerization reactions. Water uptake was measured to determine the amount of water needed for incipient wetness impregnation of metal salt onto the extrudates. Taking 95%-98% of the water uptake, the amount of stock metal salt solution for dilution was subtracted to determine the amount of water required to form a diluted metal salt solution for impregnation. In this example, the water uptake was 0.2 ml/g of extrudate. 50 g of extrudate was impregnated with 6.5 g of 3.8% Pt solution of H$_2$PtCl$_6$, diluted with 3.3 g of water. The amount of Pt solution was chosen to target a 0.5 wt. % Pt loading upon the extrudates. The solution was sprayed onto the dried extrudates. The extrudates were then dried at 120° C. for 2 hours. The extrudates were then calcined in air at 300° C. for 3 hours to produce the oxide form of the Pt salt. The Pt dispersion upon the extrudates ranged between 30% and 45%, as measured via CO chemisorption. The extrudates were reduced under hydrogen at 180° C. to 220° C. for 2 to 3 hours to prepare the active form of the catalyst.

Table 8 below provides characterization data for the 16 wt. % W Catalyst and the 13 wt. % W Catalyst. Surface area was determined by N$_2$ BET adsorption/desorption isotherms. NH$_3$ uptake was measured gravimetrically. The tungsten (W) surface density was calculated from (a) the measured W content (wt. %) obtained by X-ray fluorescence and (b) the measured surface area obtained by N$_2$ BET. X-ray diffraction peaks were determined using Cu Kα radiation. The following approximate 2θ peak positions are characteristic: m-WO$_3$=24.4°, m-ZrO$_2$=28.4°, and tetragonal ZrO$_2$ (t-ZrO$_2$)=30.2°.

TABLE 8

| Average Values | 16 wt. % W Catalyst | 13 wt. % W Catalyst |
|---|---|---|
| XRD Peak Height Ratio m-WO$_3$:m-ZrO$_2$ | 0.90 | 0.31 |
| Total Surface Area (m$^2$/g) | 82 | 86 |
| NH$_3$ Uptake (mmol/g) | 0.14 | 0.17 |
| W Surface Density (W atoms/nm$^2$) | 6.6 | 5.1 |

TABLE 8-continued

| Average Values | 16 wt. % W Catalyst | 13 wt. % W Catalyst |
|---|---|---|
| Wt. % Zr | 54.9 | 56.1 |
| Wt. % W | 15.6 | 13.0 |
| Wt. % Fe | 0.59 | 0.63 |
| Wt. % Pt | 0.54 | 0.59 | n-Heptane isomerization. Isomerization of n-heptane was conducted under the following conditions for each catalyst: a temperature of 170° C., 180 psig, 3 hr$^{-1}$ WHSV, and a H$_2$:hydrocarbon ratio of 2:1. Catalyst activation was carried out as follows: heat at 300° C. under 100 sccm N$_2$ for 1 hour and then heat under 100 sccm H$_2$ at 350 psig at 220° C. for 24 hours.

Mixed Feed Isomerization. A mixed feed comprising 15% n-pentane, 55% n-hexane, and 30% n-heptane (w/w) was isomerized under similar conditions for each catalyst.

Figure 17A:
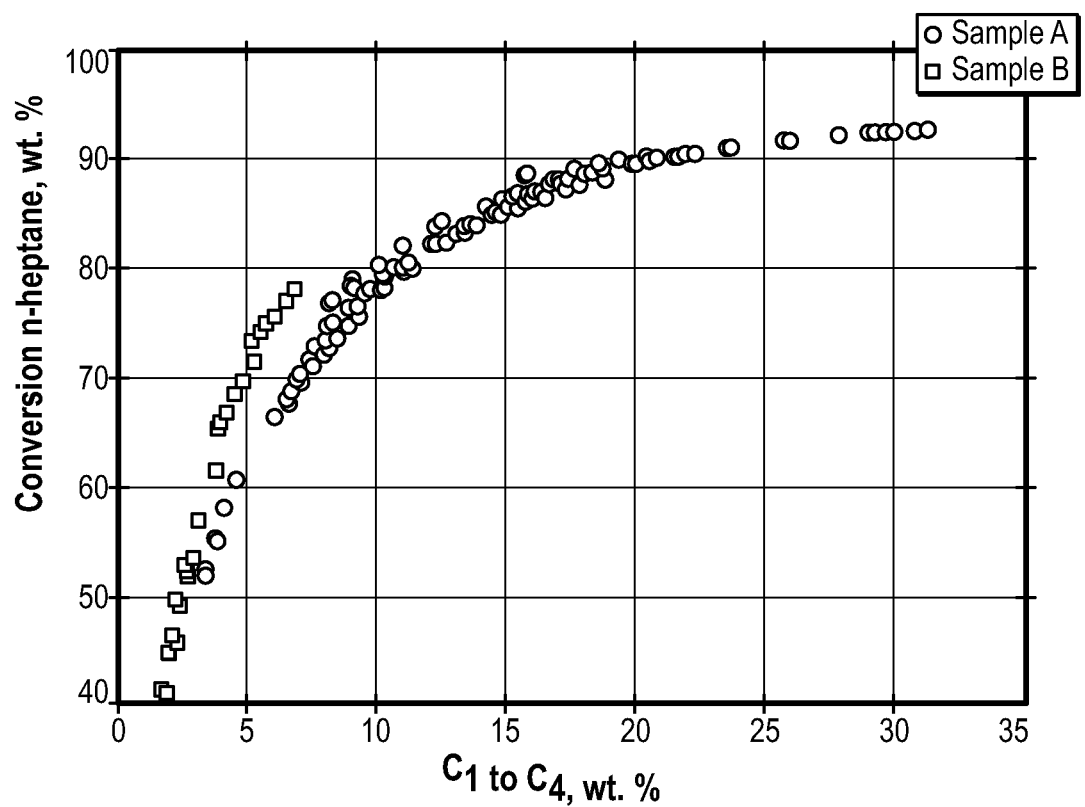
FIG. 17A is a graph showing n-heptane conversion as a function of cracking yield obtained under isomerization reaction conditions in the presence of various platinum-impregnated tungstated zirconium oxide catalysts.
Figure 17B:
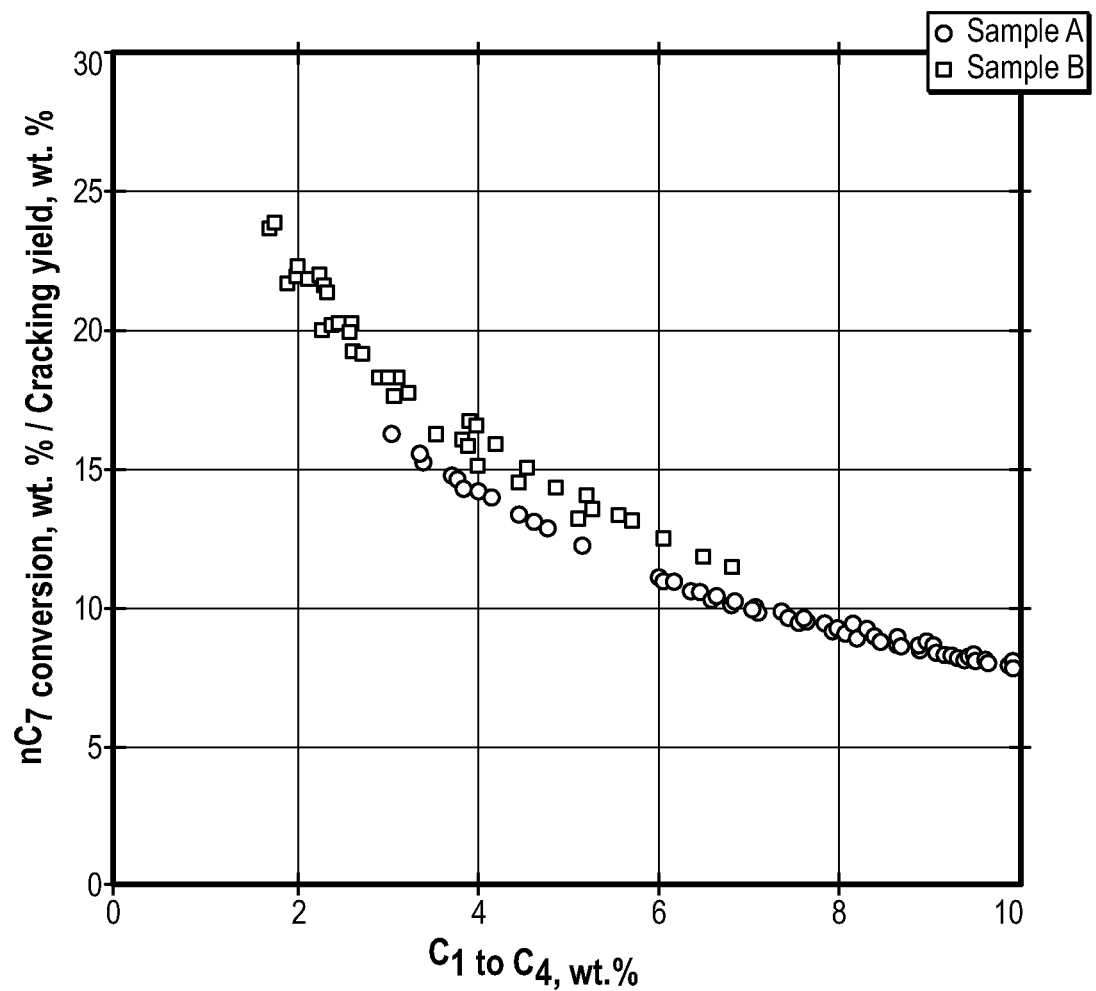
FIG. 17B is a graph showing the ratio of n-heptane conversion:cracking yield as a function of cracking yield in the presence of various platinum-impregnated tungstated zirconium oxide catalysts.
Figure 18:
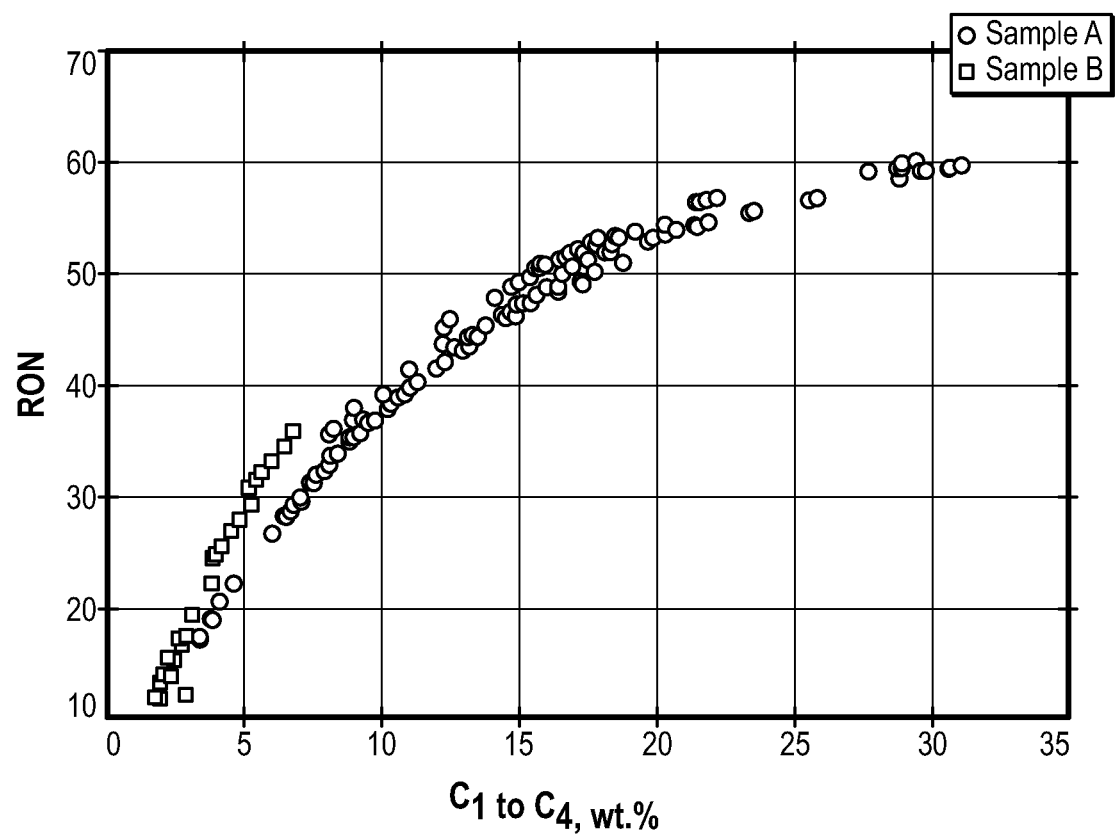
FIG. 18 is a graph showing research octane number (RON) for n-heptane conversion as a function of cracking yield under isomerization reaction conditions in the presence of various platinum-impregnated tungstated zirconium oxide catalysts.

Example 12: Isomerization of n-Heptane with 16 wt. % W Catalyst and 13 wt. % W Catalyst. The 16 wt. % W and 13 wt. % W mixed metal oxides impregnated with Pt were analyzed under similar isomerization reaction conditions for n-heptane in a fixed bed arrangement. FIG. 17A is a graph showing n-heptane conversion as a function of cracking yield obtained under isomerization reaction conditions in the presence of various platinum-impregnated tungstated zirconium oxide catalysts. Cracking yield is expressed in terms of C$_1$-C$_4$ yield. The data in FIG. 17A may be plotted alternately in terms of the ratio n-heptane conversion:cracking yield. FIG. 17B is a graph showing the ratio of n-heptane conversion:cracking yield as a function of cracking yield in the presence of various platinum-impregnated tungstated zirconium oxide catalysts. FIG. 18 is a graph showing research octane number (RON) for n-heptane conversion as a function of cracking yield under isomerization reaction conditions in the presence of various platinum-impregnated tungstated zirconium oxide catalysts. At equal cracking yields, conversion of n-heptane was higher for the 13 wt. % W mixed metal oxide compared to the 16 wt. % W mixed metal oxide, and the RON was also higher for the 13 wt. % W mixed metal oxide compared to the 16 wt. % W mixed metal oxide. Higher ratios of n-heptane conversion:cracking yield were obtained for the 13 wt. % W mixed metal oxide. RON was determined as specified in Ghosh, et al., *Ind. Eng. Chem. Res.*, 2006, pp. 337-345, 45.

Figure 19:
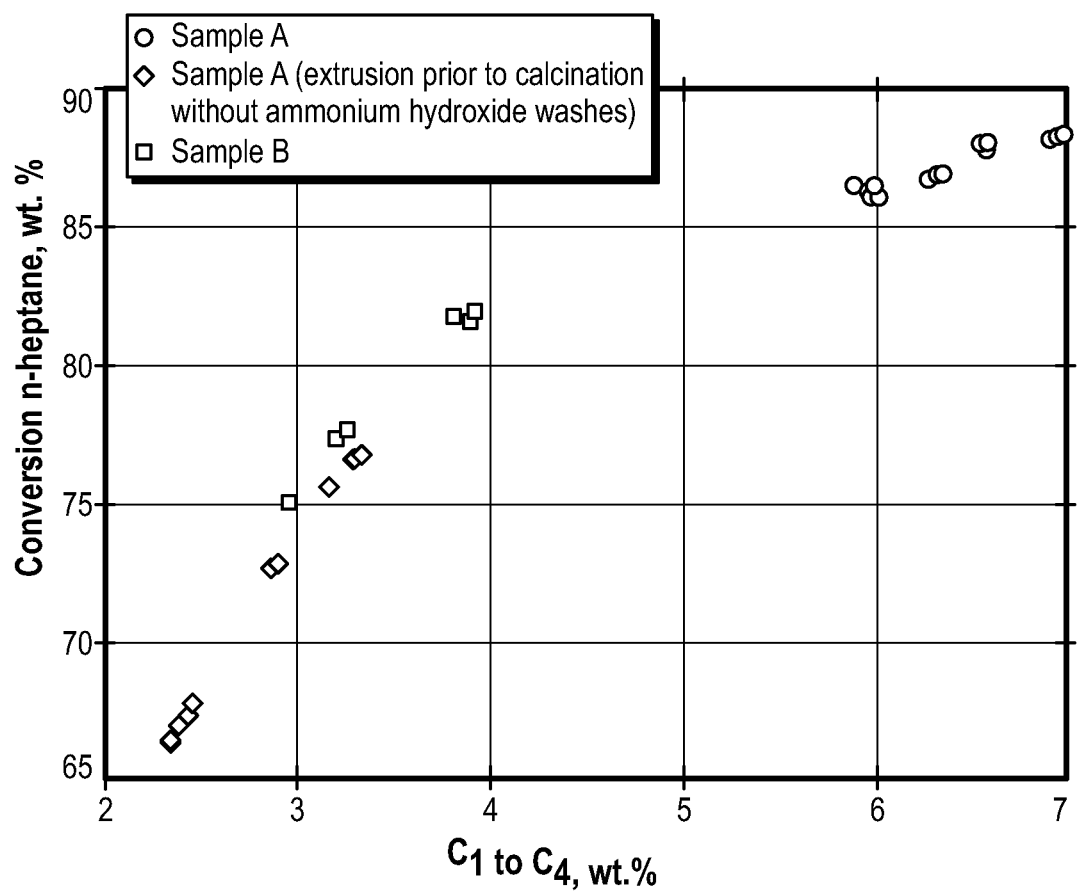
FIG. 19 is a graph showing n-heptane conversion in a C5-C7 normal paraffin blend as a function of cracking yield under isomerization reaction conditions in the presence of various platinum-impregnated tungstated zirconium oxide catalysts.

Example 13: Isomerization of a C$_5$-C$_7$ Normal Paraffin Blend with 16 wt. % W Catalyst and 13 wt. % W Catalyst. The 16 wt. % W and 13 wt. % W mixed metal oxides impregnated with Pt were analyzed under similar isomerization reaction conditions for a C$_5$-C$_7$ normal paraffin blend in a fixed bed arrangement. FIG. 19 is a graph showing n-heptane conversion in a C$_5$-C$_7$ normal paraffin blend as a function of cracking yield under isomerization reaction conditions in the presence of various platinum-impregnated tungstated zirconium oxide catalysts. Again, at equal cracking yields, the conversion of n-heptane was higher for the 13 wt. % mixed metal oxide compared to the 16 wt. % mixed metal oxide.

Many alterations, modifications, and variations will be apparent to one having ordinary skill in the art in light of the foregoing description without departing from the spirit or scope of the present disclosure and that when numerical limits and numerical upper limits are listed herein, ranges from any lower limit to any upper limit are contemplated.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A method comprising:
providing a first bifunctional mixed metal oxide catalyst comprising a first bifunctional mixed metal oxide impregnated with noble metal, the first bifunctional mixed metal oxide catalyst comprising about 40 wt. % to about 70 wt. % zirconium, a first amount of tungsten, and about 0.01 wt. % to about 5 wt. % variable oxidation state metal, each based on total mass of the mixed metal oxide;
providing a second bifunctional mixed metal oxide catalyst comprising a bifunctional mixed metal oxide impregnated with a noble metal, the second bifunctional mixed metal oxide catalyst comprising a second amount of tungsten, the first amount of tungsten, relative to a weight of the first bifunctional mixed metal catalyst, being higher than the second amount of tungsten relative to a weight of the second bifunctional mixed metal catalyst,
wherein the second bifunctional mixed metal oxide catalyst comprises about 40 wt. % to about 70 wt. % zirconium and about 0.01 wt. % to about 5 wt. % variable oxidation state metal, each based on total mass of the bifunctional mixed metal oxide, and an amount of tungsten effective to isomerize n-heptane to one or more branched paraffins at about 70% to about 80% conversion under isomerization reaction conditions with a selectivity ratio of conversion to cracking for n-heptane of about 11 or greater;
sequentially contacting the first bifunctional mixed metal oxide catalyst and the second bifunctional mixed metal oxide catalyst under the isomerization reaction conditions with a feed mixture comprising at least one $C_{7+}$ normal paraffin; and
obtaining one or more branched paraffins formed from the at least one $C_{7+}$ normal paraffin under the isomerization reaction conditions.

2. The method of claim 1, wherein the selectivity ratio ranges from about 11 to about 14.

3. The method of claim 1, wherein the first amount of tungsten is effective to isomerize n-heptane at about 70% to about 80% conversion with a cracking yield for n-heptane of about 8 wt. % or less.

4. The method of claim 1, wherein the first amount of tungsten effective to isomerize n-heptane ranges from about 13 wt. % to about 16 wt. %, based on total mass of the bifunctional mixed metal oxide.

5. The method of claim 1, wherein the variable oxidation state metal comprises Fe.

6. The method of claim 1, wherein the first bifunctional mixed metal oxide catalyst and the second bifunctional mixed metal oxide catalyst are arranged in a stacked bed configuration.

7. The method of claim 1, wherein the feed mixture does not contain normal paraffins larger than $C_8$.

8. The method of claim 1, wherein the feed mixture comprises at least $C_5$-$C_7$ normal paraffins.

9. The method of claim 1, wherein the feed mixture further comprises one or more branched paraffins.

* * * * *